US012042602B2

(12) United States Patent
Hobson et al.

(10) Patent No.: US 12,042,602 B2
(45) Date of Patent: Jul. 23, 2024

(54) NASAL CANNULA

(71) Applicant: Fisher & Paykel Healthcare Limited, Auckland (NZ)

(72) Inventors: Nicholas Alexander Hobson, Auckland (NZ); Steven Charles Korner, Auckland (NZ); Craig Karl White, Auckland (NZ); Jason Peter van Beurden, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1010 days.

(21) Appl. No.: 16/239,433

(22) Filed: Jan. 3, 2019

(65) Prior Publication Data

US 2019/0134336 A1 May 9, 2019

Related U.S. Application Data

(63) Continuation of application No. 14/679,322, filed on Apr. 6, 2015, now Pat. No. 10,207,071, which is a
(Continued)

(51) Int. Cl.
*A61M 16/00* (2006.01)
*A61M 16/06* (2006.01)
(Continued)

(52) U.S. Cl.
CPC .... *A61M 16/0666* (2013.01); *A61M 16/0003* (2014.02); *A61M 16/0066* (2013.01);
(Continued)

(58) Field of Classification Search
CPC .......... A61M 16/0666; A61M 16/0672; A61M 16/0677; A61M 16/00
See application file for complete search history.

(56) References Cited

U.S. PATENT DOCUMENTS 2,735,432 A 2/1956 Hudson
3,400,714 A * 9/1968 Sheridan ........... A61M 16/0666
128/207.18
(Continued)

FOREIGN PATENT DOCUMENTS

AU 2009243444 6/2010
CA 2686747 6/2010
(Continued)

OTHER PUBLICATIONS

Office Action received in Canadian Application No. 3011836, dated Feb. 18, 2021.
(Continued)

*Primary Examiner* — Michael R Reid
*Assistant Examiner* — Tyler A Raubenstraw
(74) *Attorney, Agent, or Firm* — Knobbe, Martens, Olson & Bear LLP

(57) ABSTRACT

A nasal cannula arrangement for use as part of systems for delivery respiratory gases to a patient is disclosed. The nasal cannula arrangement includes a manifold part adapted to receive gases from a delivery conduit. The manifold includes one but preferably a pair of prongs extending upward and curving towards the rear of the manifold. The prongs are inserted into the nostrils of the patient and deliver gases to a patient. The prongs have a cut out on the rear side of the prongs. The cut out forms a gases outlet in the prongs and are shaped such that the area of the cut out area is greater than the cross sectional area of the prongs at the entry point to the prongs.

15 Claims, 11 Drawing Sheets

Related U.S. Application Data continuation of application No. 12/628,454, filed on Dec. 1, 2009, now Pat. No. 8,997,747.

(60) Provisional application No. 61/118,750, filed on Dec. 1, 2008.

(51) Int. Cl.
*A61M 16/10* (2006.01)
*A61M 16/12* (2006.01)
*A61M 16/16* (2006.01)

(52) U.S. Cl.
CPC .... *A61M 16/0069* (2014.02); *A61M 16/0672* (2014.02); *A61M 16/0683* (2013.01); *A61M 16/109* (2014.02); *A61M 16/1095* (2014.02); *A61M 16/122* (2014.02); *A61M 16/161* (2014.02); *A61M 16/16* (2013.01); *A61M 2202/0208* (2013.01); *A61M 2205/33* (2013.01); *A61M 2205/3368* (2013.01); *A61M 2205/50* (2013.01); *A61M 2205/52* (2013.01)

(56) References Cited

U.S. PATENT DOCUMENTS

| | | | |
|---|---|---|---|
| 3,643,660 A * | 2/1972 | Hudson | A61M 25/02 128/207.18 |
| 4,278,082 A | 7/1981 | Blackmer | |
| 4,753,233 A | 6/1988 | Grimes | |
| 4,829,998 A | 5/1989 | Jackson | |
| 5,099,836 A * | 3/1992 | Rowland | A61M 16/0051 128/207.18 |
| 5,513,634 A | 5/1996 | Jackson | |
| 5,526,806 A | 6/1996 | Sansoni | |
| 6,431,172 B1 * | 8/2002 | Bordewick | A61M 16/0666 128/207.18 |
| 6,478,026 B1 | 11/2002 | Wood | |
| 6,561,188 B1 | 5/2003 | Ellis | |
| 6,655,385 B1 | 12/2003 | Curti et al. | |
| 6,679,265 B2 | 1/2004 | Strickland et al. | |
| 7,047,974 B2 * | 5/2006 | Strickland | A61M 16/0833 128/207.18 |
| 7,178,525 B2 | 2/2007 | Matula, Jr. et al. | |
| 7,353,826 B2 * | 4/2008 | Sleeper | A61M 16/0833 128/207.18 |
| 7,406,966 B2 * | 8/2008 | Wondka | A61M 16/0009 128/207.18 |
| 7,493,902 B2 | 2/2009 | White et al. | |
| 8,997,747 B2 | 4/2015 | Hobson et al. | |
| 10,207,071 B2 | 2/2019 | Hobson et al. | |
| 2002/0096173 A1 | 7/2002 | Berthon-Jones et al. | |
| 2003/0200970 A1 | 10/2003 | Stenzler et al. | |
| 2004/0065330 A1 | 4/2004 | Landis | |
| 2004/0226566 A1 * | 11/2004 | Gunaratnam | A61M 16/08 128/207.18 |
| 2004/0261797 A1 * | 12/2004 | White | A61M 16/0003 128/206.11 |
| 2005/0028822 A1 | 2/2005 | Sleeper | |
| 2005/0076913 A1 * | 4/2005 | Ho | A61M 16/0633 128/207.13 |
| 2005/0126574 A1 * | 6/2005 | Wood | A61M 16/0666 128/207.18 |
| 2006/0266359 A1 | 11/2006 | Van Beurden et al. | |
| 2007/0113849 A1 | 5/2007 | Matthews et al. | |
| 2007/0283957 A1 | 12/2007 | Schobel (nee Bauer) et al. | |
| 2008/0121230 A1 * | 5/2008 | Cortez | A61M 16/0688 128/207.18 |
| 2008/0190436 A1 | 8/2008 | Jaffe et al. | |
| 2009/0173349 A1 | 7/2009 | Hernandez et al. | |
| 2009/0320851 A1 | 12/2009 | Selvarajan et al. | |
| 2015/0209542 A1 | 7/2015 | Hobson et al. | |

FOREIGN PATENT DOCUMENTS

| | | |
|---|---|---|
| CA | 2938743 C | 3/2020 |
| CA | 3011836 C | 4/2022 |
| JP | 2005-40589 | 2/2005 |
| JP | 2006-518231 | 8/2006 |
| JP | 2006-239424 | 9/2006 |
| JP | 2007-518451 | 7/2007 |
| JP | 2007-520321 | 7/2007 |
| JP | 2008-541955 | 11/2008 |
| JP | 5281562 | 9/2013 |
| WO | WO 2003/066145 A1 | 8/2003 |
| WO | WO 2004/073778 A1 | 9/2004 |
| WO | WO 2005/014080 A2 | 2/2005 |
| WO | WO 2005/016402 A2 | 2/2005 |
| WO | WO 2005/018524 A2 | 3/2005 |
| WO | WO 2005/076874 A2 | 8/2005 |
| WO | WO 2006/130903 A1 | 12/2006 |
| WO | WO 2007/033347 | 3/2007 |
| WO | WO 2007/064660 | 6/2007 |
| WO | WO 2008/007985 | 1/2008 |
| WO | WO 2008/011682 A1 | 1/2008 |
| WO | WO 2008/014543 | 2/2008 |
| WO | WO 2008/019294 | 2/2008 |
| WO | WO 2008/060295 | 5/2008 |
| WO | WO 2008/060523 | 5/2008 |
| WO | WO 2008/063179 A1 | 5/2008 |

OTHER PUBLICATIONS

Australian Examination Report; dated Jul. 29, 2016; 3 pages.
Canadian Examination Report; dated Apr. 25, 2017; 4 pages.
Examination Report and letter with English translation of examination report; dated Dec. 16, 2011; 12 pages.
German Examination Report; dated Aug. 23, 2016; 6 pages.
German Office Action English Translation; dated Oct. 9, 2013; 7 pages.
Japanese Examination and English Translation Report Letter; dated Jan. 8, 2014; 9 pages.
Search Report and Written Opinion FR0958568; dated Dec. 16, 2010, 5 pages.
Translation of Japanese Office Action dated Sep. 27, 2012 for Patent Application No. 2009-288391 in 2 pages.
Examination Report received in Australian Application No. 2020201032, dated Jan. 21, 2021, in 5 pages.
Optiflow™ Humidified Nasal Interface Brochure, 2 pages, Jul. 2006.
Technical Drawing of the Optiflow™ Humidified Nasal Interface made by Fisher & Paykel Healthcare and pictured in the pages of the brochure listed as cite No. 3.

* cited by examiner

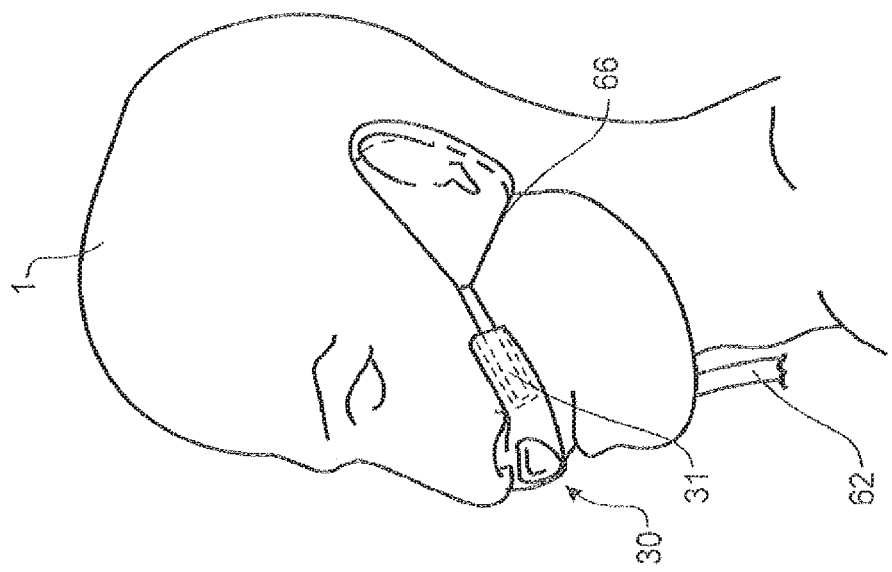
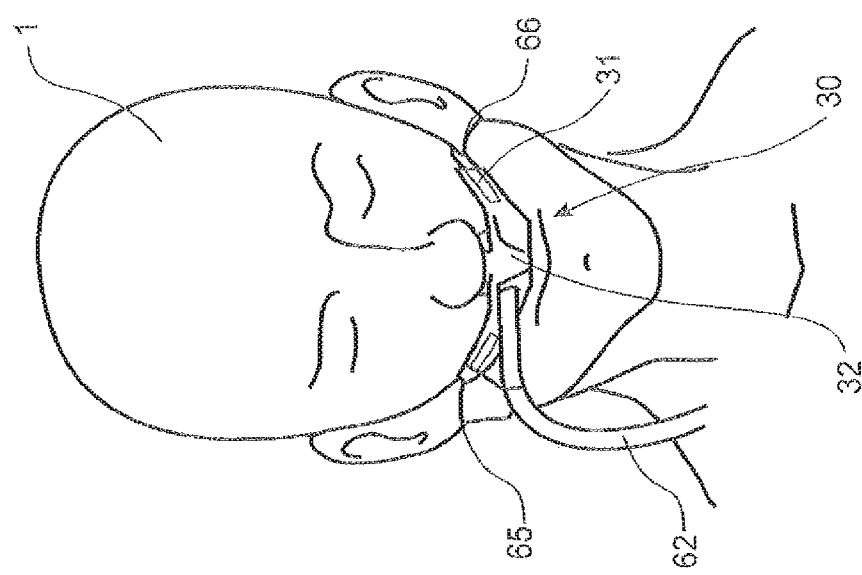
FIGURE 3

NASAL CANNULA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to nasal cannula arrangements for supplying gases to a user via the nasal passages. The present invention also relates to a system which provides gases to a patient or user via the nasal passages. The present invention also relates to a method of supplying gases to a user via the nasal passages.

Description of the Related Art

The prior art includes a wide variety of interfaces for supplying gases to a patient. These interfaces are frequently used for delivering a stream of gases to a person being treated for a sleep disorder, or for delivery of supplementary gases to a user who is breathing unaided, but who requires these supplementary gases. These users typically wear the interface in a hospital Intensive Care Unit (ICU), other hospital wards or a home sleeping environment. Comfort even under conditions of patient movement is a major consideration.

The following are examples of interface types known in the prior art.

The prior art includes a nasal cannula interface. A typical nasal cannula interface includes a plenum portion and entry tubing or a manifold section (symmetric or single sided) that rests against the upper lip of the user in use, and a pair of open-ended prongs, which protrude from the entry tubing and extend into the nostrils of the user in use to supply the patient with gases. Generally, but not always, these prongs are sized and shaped so that they do not seal against the nostrils of a patient. Nasal cannulae are used because these are advantageous in certain situations. For example, in circumstances where a patient is breathing normally, but requires supplementary gases such as supplementary oxygen. The existing market for nasal cannula is well serviced by devices suitable for delivery of gases in the 0 to 5 litres per minute range. These devices are typically supported by a double entry lumen of small diameter (2-3 mm range) that supplies both sides of the nasal cannula and provides even or equal airflow to each nasal prong. These devices work well for the delivery of dry gas flows of between 0 to 5 litres per minute, when the patient is self-breathing, and it is not necessary for the cannula prongs to seal against the nares of a user. A user will entrain the supplementary gases provided from the cannula along with atmospheric air as they inhale normally.

An example of a nasal cannula interface that seals against the nostrils is the Nasal-Aire interface made by Innomed, where gases are provided to the interface and the prongs by conduits or hoses that extend from the users nose across their cheeks, over their ears and around the back of their head.

WO 2008/060295 describes a non-sealing cannula that includes nasal prongs. There are many configurations described. The nasal prongs are adapted to deliver air to a patient's nasal passage and the different embodiments of prongs described include various external features, and may include passages that pass through the wall of the prongs to allow sensors or similar to measure the properties of gases in the prongs.

The prior art also includes several other types of interface, which are included here for general context, but which are not directly relevant. These are outlined briefly below.

A nasal mask, which includes a perimeter seal that seals across, down each cheek alongside the nose and along the surface of the upper lip. The entire enclosed space is pressurised and the recipient may inhale the pressurised gas from the enclosed space. An example is the Flexifit 405 nasal mask sold by Fisher & Paykel Healthcare.

A full face mask, which includes a perimeter seal that extends across the bridge of the nose downward along each cheek beside the nose to the jaw and along the jaw below the lower lip. The perimeter thereby encloses both the nose and mouth. The entire space within the mask frame is pressurised. The recipient may breathe the pressurised gas from the space through either the nose or mouth. An example is the Hexifit 431 interface sold by Fisher & Paykel Healthcare.

An oral interface including an oral appliance that fits within the user's mouth. An example is the Fisher & Paykel Healthcare Oracle interface.

Nasal pillows, which are intended to seal around the perimeter of a user's wires in use, and deliver a stream of pressurised gases to the nasal cavity of a user. A number of different types of nasal pillow are described and shown in WO 2008/014543.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide a nasal interface which goes some way to overcoming the disadvantages of the prior art or which will at least provide the industry and public with a useful alternative.

SUMMARY OF THE INVENTION

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In a first aspect the invention can be said to broadly consist in a nasal cannula arrangement for use as part of a system for delivering respiratory gas to a patient, said system of the type that has a gases source adapted to provide a stream of gases to the nares of a user in use, and a delivery conduit that in use connects between said gases source and said nasal cannula arrangement, said nasal cannula arrangement comprising: a gases inlet manifold part adapted in fluid connection with said delivery conduit in use, so that said stream of gases is delivered into said manifold part, at least one and preferably a pair of nasal prongs in fluid connection with said gases inlet manifold part and adapted to be inserted into the nares of said user, said stream of gases passing through said gases inlet manifold part and through said prongs, said nasal prong or prongs having a gases exit cut-out on the rear side of said prong or prongs, said gases exit cut-out having a cross-sectional area greater than the cross-sectional area of said prong at or close to the point of entry of said gases to said prong or prongs.

In a second aspect the invention may broadly be said to consist in a system for delivering respiratory gases to a patient, said system comprising a gas source unit, adapted to provide a stream of gases, a patient interface, a delivery conduit which may or may not also have a secondary gases inlet conduit, adapted to receive respiratory gases from said gas source and carry respiratory gases from said gas source to said patient interface, and a nasal cannula arrangement comprising: a gases inlet manifold part adapted to form a fluid connection with said delivery conduit in use, so that said stream of gases is delivered into said manifold part, at least one and preferably a pair of nasal prongs in fluid connection with said gases inlet manifold part and adapted to be inserted into the nares of said user, said stream of gases passing through said gases inlet manifold part and through said prongs, said nasal prong or prongs having a gases exit cut-out on the rear side of said prong or prongs, said gases exit cut-out having a cross-sectional area greater than the cross-sectional area of said prong at or close to the point of entry of said gases to said prong or prongs.

In a third aspect the invention may broadly be said to consist in a nasal cannula arrangement for use as part of a system for delivering respiratory gas to a patient, said system of the type that comprises a gases source adapted to provide a stream of gases, and a delivery conduit that in use connects between said gases source and said nasal cannula arrangement, said nasal cannula arrangement comprising: a manifold section connected to one end of said delivery conduit so that in use said stream of gases is delivered from said delivery conduit to said manifold section, a pair of carrier tubes connected to said manifold section, so that said stream of gases is delivered from said manifold section to said carrier tubes, a pair of nasal prongs connected one each to each of said carrier tubes, said nasal prongs adapted to be inserted into a patient's nares, said stream of gases passing through the carrier tubes, through the nasal prongs and into the patient's nares, each of said nasal prongs having a gases exit cut-out on the rear side of said prong or prongs, said gases exit cut-out having a cross-sectional area greater than the cross-sectional area of said prong at or close to the point of entry of said gases to said prong or prongs.

In a fourth aspect the invention may broadly be said to consist in a nasal cannula arrangement for use as part of a system for delivering respiratory gas to a patient, said system of the type that comprises a gases source adapted to provide a stream of gases to the nares of a user in use, and a delivery conduit that in use connects between said gases source and said nasal cannula arrangement, said nasal cannula arrangement comprising: a gases inlet manifold part adapted to form a fluid connection with said delivery conduit in use, so that said stream of gases is delivered into said manifold part, at least one and preferably a pair of nasal prongs in fluid connection with said gases inlet manifold part and adapted to be inserted into the nares of said patient in use, said stream of gases passing in use through said gases inlet manifold part and said nasal prongs, and into said users nares, each or both of said nasal prong or prongs having a gases exit cut-out on the rear side of said prong or prongs, said gases exit cut-out having a cross-sectional area greater than the cross-sectional area of said prong at or close to the point of entry of said gases to said prong or prongs, and wherein said at least one or both of said nasal prong or prongs is shaped so that the velocity of gases exiting said prong is reduced in comparison to the velocity of gases at or close to the point of entry to said prong.

In a fifth aspect the invention may broadly be said to consist in a nasal cannula arrangement for use as part of a system for delivering respiratory gas to a patient, said system of the type that comprises a gases source adapted to provide a stream of gases to the nares of a user in use, and a delivery conduit that in use connects between said gases source and said nasal cannula arrangement, said nasal cannula arrangement comprising: a gases inlet manifold part adapted to form a fluid connection with said delivery conduit in use, so that said stream of gases is delivered into said manifold part, at least one and preferably a pair of nasal prongs in fluid connection with said gases inlet manifold part and adapted to be inserted into the nares of said patient in use, said stream of gases passing in use through said gases inlet manifold part and said nasal prongs, and into said users nares, each or both of said nasal prong or prongs having a gases exit cut-out on the rear side of said prong or prongs, said gases exit cut-out having a cross-sectional area greater than the cross-sectional area of said prong at or close to the point of entry of said gases to said prong or prongs, and wherein said at least one or both of said nasal prong or prongs is shaped, or sized, or shaped and sized, so that said stream of gases is generally directed towards the back of the patient's nasal passage.

In a sixth aspect the invention may broadly be said to consist in a method of providing a stream of gases to a user for therapeutic purposes, comprising the steps of: 1. fitting said user with a nasal cannula arrangement, 2. connecting said nasal cannula arrangement to a patient interface which in use holds said nasal cannula arrangement in position on said user, 3. connecting either said patient interface or alternatively connecting said nasal cannula arrangement directly to a gases delivery system of the type that comprises a gases source adapted to provide a stream of gases, and a delivery conduit that in use connects between said gases source and said nasal cannula arrangement, and using said system to deliver a stream of gases to said nasal cannula arrangement, said nasal cannula arrangement comprising: a gases inlet manifold part adapted to form a fluid connection with delivery conduit in use, so that said stream of gases is delivered into said manifold part, at least one and preferably a pair of nasal prongs in fluid connection with said gases inlet manifold part and adapted to be inserted into the nares of said user, said stream of gases passing through said gases inlet manifold part and through said prongs, said nasal prong or prongs having a gases exit cut-out on the rear side of said prong or prongs, said gases exit cut-out having a cross-sectional area greater than the cross-sectional area of said prong at or close to the point of entry of said gases to said prong or prongs.

In a seventh aspect the invention may broadly be said to consist in a nasal cannula arrangement for use as part of a system for delivering respiratory gas to a patient, said system of the type that comprises a gases source adapted to provide a stream of gases to the mires of a user in use, and a delivery conduit that in use connects between said gases source and said nasal cannula arrangement, said nasal cannula arrangement comprising: a gases inlet manifold part adapted to form a fluid connection with said delivery conduit in use, so that said stream of gases is delivered into said manifold part, at least one and preferably a pair of nasal prongs in fluid connection with said gases inlet manifold part and adapted to be inserted into the nares of said patient in use, said stream of gases passing in use through said gases inlet manifold part and said nasal prongs, and into said users nares, each or both of said nasal prong or prongs having a gases exit cut-out on the rear side of said prong or prongs, said gases exit cut-out having a cross-sectional area greater than the cross-sectional area of said prong at or close to the point of entry of said gases to said prong or prongs, and wherein said at least one or both of said nasal prong or prongs is shaped so that the velocity of gases exiting said prong is reduced in comparison to the velocity of gases at or close to the point of entry to said prong, and so that said stream of gases is generally directed towards the back of the patient's nasal passage.

In an eighth aspect the invention may broadly be said to consist in a nasal cannula arrangement for use as part of a system for delivering respiratory gas to a patient, said system of the type that comprises a gases source adapted to provide a stream of gases to the nares of a user in use, and a delivery conduit that in use connects between said gases source and said nasal cannula arrangement, said nasal cannula arrangement comprising: a gases inlet manifold part adapted to form a fluid connection with said delivery conduit in use, so that said stream of gases is delivered into said manifold part, at least one and preferably a pair of nasal prongs in fluid connection with said gases inlet manifold part and adapted to be inserted into the nares of said user, said stream of gases passing through said gases inlet manifold part and through said prongs, each prong having an upstream transition section and a downstream transition section, connecting the horizontally oriented manifold with upwardly oriented prong, wherein said upstream transition section having a shallow curve relative to the downstream transition section.

Preferably said cannula arrangement includes a face mount part that rests against a user's face in use, said face mount part including a pair of side straps extending from said face mount part.

Preferably said face mount part stabilises said cannula arrangement on said user's face in use by resting against the user's face.

Preferably said cut-out extends between halfway and two-thirds of the way along said nasal prong, said cut-out measured from the top tip of said nasal prong.

Alternatively said cut-out extends less than halfway along the nasal prong, said cut-out measured from the top tip of said nasal prong.

Alternatively said cut-out extends the entire length of the nasal prongs.

Preferably said cut-out has a height of between 3 mm and 15 mm.

Preferably said gases exit cut-out is oval in shape, when viewed from the rear of said nasal cannula arrangement.

Alternatively said gases exit cut-out is rectangular in shape, when viewed from the rear of said nasal cannula arrangement.

Alternatively said cut-out is triangular in shape, when viewed from the rear of said nasal cannula arrangement.

Preferably said nasal prongs are angled between 5 and 20 degrees inward relative to a vertical planar line which bisects said face mount part.

Preferably said nasal prongs are angled 15 degrees inward relative to a vertical planar line which bisects said face mount part.

Preferably the edges of said gases exit cut-out are shaped cut-out conform to a surface that substantially has a reverse S-shape, said S-shape aligned substantially vertically.

Preferably the lower edge of said surface cuts across the rear of said prongs to create said cut-out, said surface being a reverse S-shape to obtain the ideal cut-out shape.

Preferably said at least one nasal prong includes a reinforcing feature.

Preferably said reinforcing feature is located on the front face of said nasal prong and is adapted to help prevent the nasal prong from collapsing under compressive or tensile forces.

Preferably said reinforcing feature is formed as a substantially vertical ridge or spine running at least part of the way along the front face of said nasal prong.

Alternatively said at least one nasal prong includes a reinforcing feature on the inner surface of the front wall of said nasal prong, to aid in preventing the nasal prong from collapsing under tensile or compressive forces.

Preferably said at least one nasal prong includes at least one and preferably a plurality of ribs running across the front face of the nasal prong.

Preferably said at least one rib or ribs run across the outer surface of the front of said nasal prong.

Preferably the front part of the wall of said nasal prong wall is thicker than the back part of the wall of the nasal prong wall.

Preferably said feature or ribs or both are formed integrally with the nasal prong.

Alternatively said feature or ribs or both are separately attached to said prong after said prong is formed.

Preferably said nasal cannula arrangement further includes side straps adapted to allow a headgear securement assembly to be connected to said nasal cannula arrangement, so that said nasal cannula arrangement can be secured to said patients head in use.

Preferably said face mount portion, said at least one nasal prong, and at least part of said side straps are formed of a flexible polymer material, for example a thermoplastic elastomer or silicone.

Preferably said feature or ribs or both are made of the same material as said nasal prong.

Preferably said at least one or both of said nasal prong or prongs is shaped, or sized, or shaped and sized, so that said stream of gases is generally directed towards the back of the patient's nasal passage.

Preferably at least one or both nasal prong or prongs is shaped so that the velocity of gases exiting said prong is reduced in comparison to the velocity of gases at or close to the point of entry to said prong.

Preferably at least one or both of said nasal prong or prongs curve upwards and backwards towards a user in use, and said cut-out has an elongate shape along the rear and the top of said prong or prongs, so that said stream of gases is generally directed to the back of the patient's nasal passage and jetting effects are reduced.

Preferably said nasal prongs are shaped and sized so that they do not form a substantially air tight seal with the users nares in use.

Preferably the nasal prongs are suitable for delivering high flow medical gases to a patient; such that a substantial part of the patient's inhaled breath composes respiratory gases from the nasal prongs and a minimal percentage of ambient air.

Preferably the cannula arrangement includes a face mount part attached to said manifold, said face mount part resting against top lip of said patient, to stabilise said cannula on said patient's face.

Preferably said manifold section is a Y or T piece connector.

Preferably said nasal prongs are integral to the carrier conduit.

Preferably each said transition section transitioning from a horizontal to an upright orientation within an area, said area of transition defined by vertical rise and a horizontal run, said rise for said upstream and downstream transition sections being substantially equal to each other, said upstream transition section having a horizontal run being between one and two and a half times the horizontal run of said downstream transition section.

Preferably said rise and run is defined from a starting point being a tangent point of said manifold and a finishing point being the narrowest point of said prong.

Preferably said upstream transition section having a horizontal run one and half times the horizontal run of said downstream transition section.

Preferably said manifold flow chamber including an upwardly angled wall positioned opposite the upstream prong, said wall deflecting said gases stream by at least 20 degrees upward substantially toward the base of said prong.

Preferably said downstream transition section angled upward at a steeper angle than said upstream transition section.

Preferably said downstream transition section having an upward angle between 1.1 to 2.5 larger than the upward angle of said upstream transition section.

More preferably said downstream transition section having an upward angle 1.5 times greater than the upward angle of said upstream transition section.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The term "comprising" as used in the specification means "consisting at in part of". When interpreting each statement in this specification that includes the term "comprising", features other than that or those prefaced by the term may also be present. Related terms such as "comprise" and "comprises" are to be interpreted in the same manner.

BRIEF DESCRIPTION OF THE DRAWINGS

While the invention is susceptible to embodiment in different forms, specific embodiments are shown in the drawings, and described in detail. The present disclosure is to be considered an exemplification of the principles of the invention, and is not intended to limit the invention to that as illustrated and described herein.

FIG. 3 shows a front and a side view of an alternative embodiment of the patient interface in use, this alternative form having a pair of ear straps that loop around the ears of a user in use to hold the patient interface in place on the face of a user in use.

DETAILED DESCRIPTION OF THE PREFERRED EMBODIMENT

A preferred form of nasal cannula arrangement is described below with reference to use as part of a patient interface for use in a medical gases system. It should be noted that the nasal cannula arrangement can be used with any suitable system that provides a gases stream from a gases source to a patient in use. For example, it could be used as part of a system to provide supplementary oxygen to a user, with the oxygen provided from a source such as a gas bottle or wall outlet. However, it is most suited for a system that provides a heated, humidified, gases stream to a patient or user. The nasal cannula is suitable for use in the home or in a hospital environment. The nasal cannula can be varied in size (with the proportions kept generally the same) for use with users of different sizes. For example, two (or more different sizes could be produced for adult and infant users, but still fall within the scope of the present invention.

First Embodiment

Figure 1:
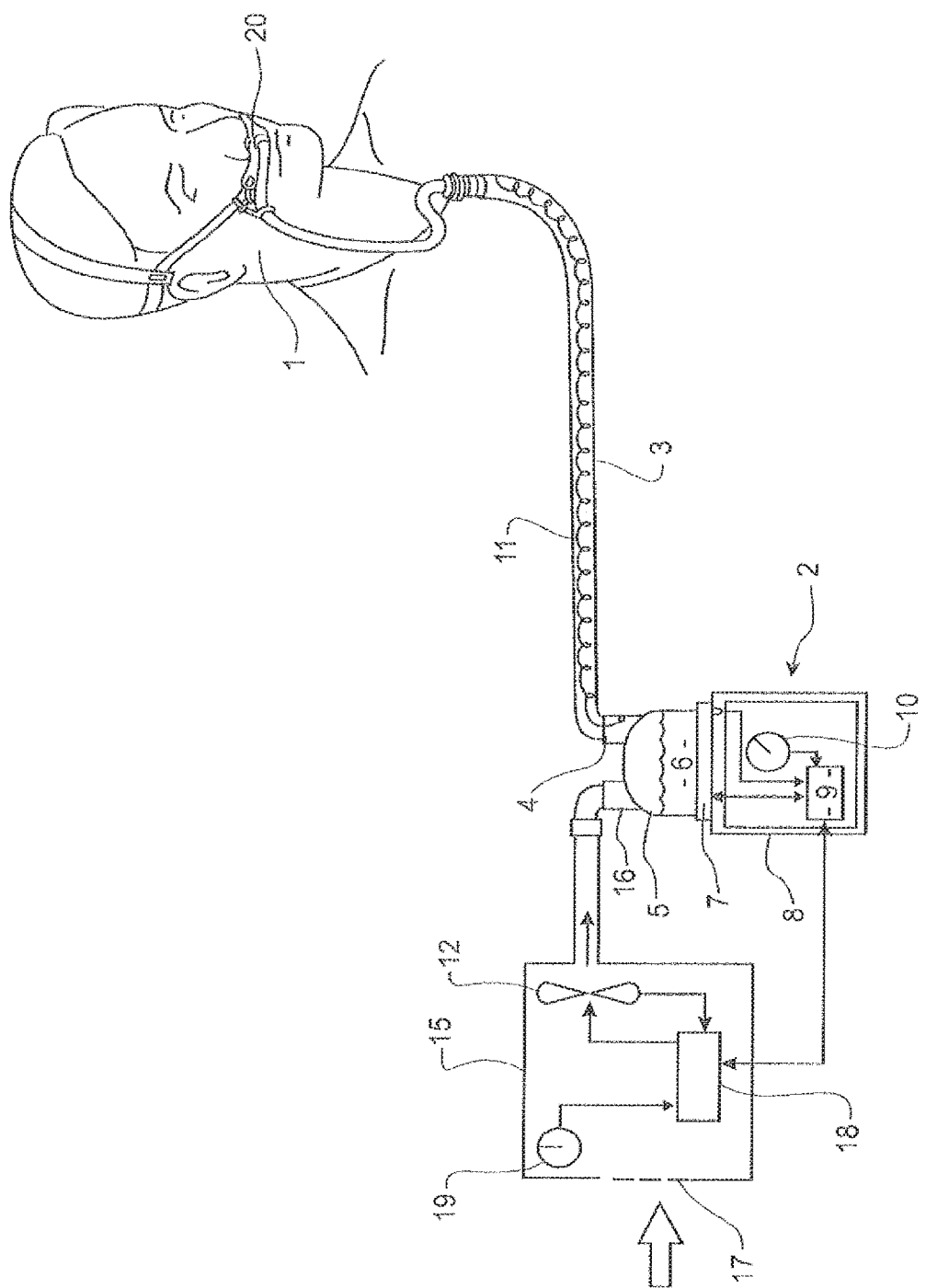
FIG. 1 shows a respiratory humidification system that includes a blower unit, a humidifier unit gaseously connected to the gases source unit, a gases supply conduit connected to an outlet of the humidifier unit, and a patient interface, the patient interface connecting between the gases supply conduit and a user so that gases can be provided to the user from the respiratory humidification system via the patient interface, the patient interface including a nasal cannula.

Referring to FIG. 1 a respiratory humidification system such as might be used with a first preferred embodiment of nasal cannula arrangement is shown. A patient or user 1 is receiving a humidified stream of gases through a patient interface 20 which includes the nasal cannula arrangement and which will be described in detail below. The patient interface 20 is connected to a delivery conduit 3, the delivery conduit 3 being connected between a humidifier unit 2 and the patient interface 20. The humidifier unit 2 consists of a humidification chamber 5 that in use contains a volume of water 6, and a base unit 8. The preferred embodiment of humidification chamber 5 is formed from a plastics material and in the preferred embodiment includes a conductive base (for example aluminium) which is in direct contact with a heater plate 7 of the humidifier base unit 8. The humidifier base unit 8 is in the preferred embodiment provided with a control mechanism or electronic controller 9 which comprises a microprocessor based controller executing computer software commands stored in the controller's memory.

In the preferred form as shown in FIG. 1, the humidifier 2 receives gases from a gas source unit 15, the gases becoming heated and humidified as they pass through the chamber 5. It should be noted that as outlined above, the gas source unit 15 could be replaced or supplemented by a wall port or a gas bottle. The gas source unit could be a gas bottle, a gas blender, a venturi device or a standard blower unit, or any other suitable system or device that supplies a gases stream. Humidified gases flow from the humidifier 2 through the delivery conduit 3 to the patient by way of the patient interface 20.

It should be noted that the system used with the nasal cannula does not require the use of a humidifier—that is, the gases stream could be dry and unheated if required. Various types of therapy can be delivered by using the nasal cannula. The preferred form of therapy will be described later. Generally breathing gases and the respiratory gases delivery system can be used with the nasal cannula. The respiratory humidification described here is just an example of the type of therapy and system the nasal cannula can be used with or as part of.

The controller 9 receives inputs from sources such as user input via dial 10, through which a user of the device may, for example, set a predetermined required value of humidity or temperature of gases supplied to the patient 1. In response to the user input or input from any other possible inputs like sensors (for example temperature or humidity sensors, not shown), the controller 9 determines when, and what level, to energise the heater plate 7 to heat the water 6 within the humidification chamber 5. As the volume of the water 6 within the humidification chamber 5 is heated, water vapour begins to fill the remaining volume of the humidification chamber 5. The gases which are provided to the humidifier unit 2 from the blower unit 15 enter the humidification chamber 5 above the surface of the water 6, and are humidified by the water vapour within the humidification chamber as they pass through the chamber 5. The heated humidified gases exit the humidification chamber 5 through an outlet 4 and are transferred to the patient interface 20 by the delivery conduit 3.

The preferred form of blower 15 is provided with a variable speed pump or fan 12 which draws air or other gases through a blower inlet 17. The speed of the pump or fan 12 is in the preferred embodiment controlled by a further control apparatus 18. Alternatively control of the pump or fan speed can be carried out by controller 9. The fan controller 18 can also be adapted to receive inputs from sensors in the system, or a user input from a control panel or control unit 19. As noted above, the blower unit 15 can be supplemented by or replaced by a gases source such as a gases bottle or a wall-mounted outlet connected to a central gases source.

The preferred form of delivery conduit 3 includes a heating element 11 to prevent condensation of humidified gases occurring within the conduit 3 ('rain out').

The preferred form of humidification system has been described above, with the nasal cannula described as being included as part of the patient interface 20. The nasal cannula will now be described in more detail with particular reference to FIGS. 2 to 5.

Patient Interface

Figure 2:
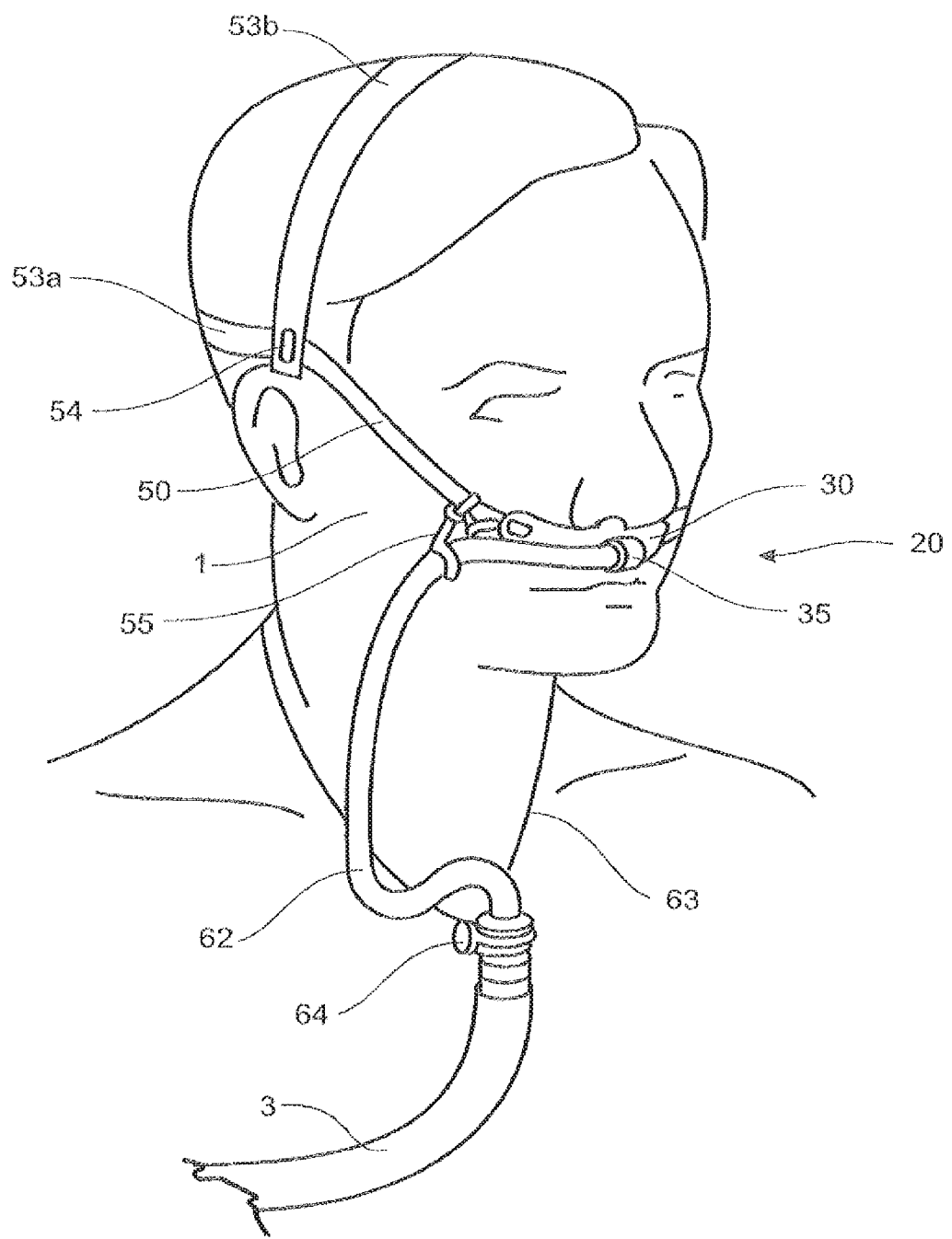
FIG. 2 shows a perspective view of the preferred embodiment of the patient interface in use on a user, the preferred form of patient interface including a secondary supply conduit which connects between the outlet end of the gases supply conduit and the nasal cannula, and a neck tie or lanyard which in use loops around the neck of a patient and connects to the supply conduit at or close to the outlet end to support the weight of the supply conduit in use, the patient interface also including a head strap for securing the patient interface to a patient's head in use.

FIG. 2 shows the first embodiment of the patient interface 20 of FIG. 1 in more detail. The patient interface 20 broadly consists of a head securement mechanism and a nasal cannula arrangement 30, and also includes a gases inlet conduit or secondary supply conduit 62. The head securement mechanism enables a user to place and maintain the nasal cannula arrangement 30 in the correct operational position. The gases inlet conduit or secondary supply conduit 62 forms a fluid or gases connection between the outlet end of the main delivery conduit 3 and the nasal cannula arrangement 30 to allow fluids or gases to flow between the main delivery conduit and nasal cannula arrangement. The secondary supply conduit 62 and detail of the main portion of the nasal cannula arrangement 30 will be described in detail below.

Head Securement

The preferred and alternative forms of head securement mechanism, which form part of the patient interface 20, will be described with particular reference to FIGS. 2 and 3. FIG. 2 shows the preferred form of the head securement mechanism, while FIG. 3 shows an alternate embodiment of the head securement mechanism.

In the preferred embodiment, the patient interface 20 is secured to the patient's head or face by a front strap 50 and rear and top straps 53a and 53b, as shown in FIG. 2. The front strap 50 in use connects with the nasal cannula arrangement 30 and the rear strap 53a and the top strap 53b connect with the front strap 50, the rear strap 53a wrapping around the top and back of the patient's head in use. The most preferred form of head strap device is adjustable to allow patients of different sizes and head shapes to use the nasal cannula arrangement 30. For example, an adjustment buckle 54 could be included which allows a patient to loosen or tighten the head strap 53.

Alternatively the patient interface is secured to the patient's head and face by a front strap 50 and a single rear strap 53a attached to the front strap 50. The rear strap may be attached to the front strap 50 via a buckle 54 or alternatively the rear strap 53a may be integral with the front strap 50. The buckle 54 allows a patient to loosen or tighten the side straps in order to achieve a comfortable fit. Alternatively the integral front and rear straps are elastic and can be stretched over a patients head. The elasticity of the straps exerts a force upon the head to hold the nasal interface in the optimal position when in use. Elastic side straps 50, 53*a* can be used with the adjustment buckle 54 or the elastic side straps 50, 53*a* may be used on their own without the buckle 54.

The head strap arrangement may also include a loop 55 which holds and supports the secondary supply conduit 62 at or close to the inlet end (described in detail below).

A neck tie or lanyard 63 may also be provided with the patient interface 20. FIG. 2 shows an example of a neck tie or lanyard 63. In the preferred embodiment the neck tie or lanyard 63 is connected to the gases inlet conduit 62 or at a location at or close to the connection between the delivery conduit 3 and the gases delivery conduit 62, supporting the weight of the delivery conduit 3 and the gases inlet conduit 62 in use. A toggle 64 is provided with the neck tie 63 to allow adjustment of the neck tie's length. The toggle 64 makes the neck tie 63 suitable for any sized patient to use the patient interface 20. The neck tie 63 supports the weight of delivery conduit 3 in use, such that the weight does not act on the user or the nasal cannula arrangement 30. The use of the neck tie 63 prevents the combined weight of the delivery conduit 3 and the gases inlet conduit 62 from pulling on the nasal cannula arrangement 30, helping to prevent the nasal prongs 33, 34 from interfering with the sensitive lining of the nasal passages, or becoming displaced or disoriented in use. The preferred embodiment of neck tie or lanyard 63 is loose fitting around the neck so as to prevent strangulation of the user. The lanyard 63 also provides a convenient way of supporting the delivery conduit 3 and the gases inlet conduit 62. This allows the patient to turn in bed without tugging or pulling on the conduit 3 and helps avoid having the gases inlet conduit 62 from overheating under the blankets. In the most preferred form the neck tie or lanyard 63 has a clip that allows the lanyard to be opened and closed by a user in order place and secure the neck tie 63 around a user's neck. The dip comprises a male and female connector that snap fit together. The clip is removed by pulling one end of the neck tie 63. The clip is easily removable and "breaks away" undoing the clip when the user pulls on one side of the neck tie. This allows the neck tie 63 to be removed quickly in an emergency situation.

An alternate embodiment of the head securement mechanism is shown in FIG. 3. The nasal cannula arrangement 30 is secured to a patients head with the aid of over the ear loops 66. The loops 66 are configured to hang over a patient's ears to support the weight of the cannula arrangement 30. The loops are attached to the nasal cannula arrangement by the side straps 31 (described below) of the nasal cannula arrangement. The ear loops are horizontally slideable relative to the straps 31. The horizontal movement capability allows a user to adjust the tightness of the ear loops to ensure the nasal cannula arrangement fits comfortably and correctly upon a user's face. The loops 66 bear the weight of the nasal cannula arrangement 30, such that the user's nasal passages are not put under undue stress because of the weight of the nasal cannula arrangement 30. The loops make the cannula arrangement 30 more comfortable to wear.

Gases Inlet Conduit

The secondary supply conduit 62 will now be described in detail. The secondary supply conduit 62 is a short length of conduit or tubing which runs between the outlet of the main delivery conduit 3 and the nasal cannula arrangement 30. In use, gases exit the main delivery conduit 3 and enter the secondary supply conduit 62, travelling along the secondary supply conduit 62 to the patient. One reason that secondary conduits such as the secondary supply conduit 62 are used is as follows: the main delivery conduit 3 is relatively heavy and cumbersome as it is used to transport gases over a reasonably long distance (from the humidifier unit 2 to a point close to the patient). The main delivery conduit 3 is therefore required to have a wall that is strong enough to support its own weight without collapsing. As the main delivery conduit 3 is therefore relatively long (e.g. 8 to 10 feet), this additional length and the thicker wall structure adds to the weight of the main delivery conduit 3. If the outlet of the main delivery conduit 3 is connected directly to the patient interface in such a manner that the user 2 is required to support this weight, this can cause discomfort to the user due to the weight of main delivery conduit acting on the user. A lighter, shorter secondary conduit (e.g. secondary supply conduit 62) running between the outlet of the main delivery conduit 3 and the patient interface 20 is used. Secondary supply conduit 62 is lighter and shorter than the main delivery conduit 3, and as outlined above, is generally used with e.g. a neck tie or lanyard 63 connected to the secondary supply conduit 62 or to the connection between the main delivery conduit 3 and the secondary supply conduit 62, to support the weight of the main delivery conduit 3 and the secondary supply conduit 62 in use.

The connection between the outlet of the main delivery conduit 3 and the inlet of the secondary supply conduit 63 is placed near to the patient to reduce torsion or pulling on the nasal cannula arrangement 30 and reduce possible heat problems or over heating close to the patient due to the heating element 11 provided in the main delivery conduit 3. In order to reduce condensate forming in the unheated secondary supply conduit 62, a conduit that has vapour transmission properties can be provided. The secondary supply conduit 62 can be integrally formed with the main delivery conduit 3 or may be attached by some connection mechanism, allowing for detachment of the secondary supply conduit 62 from the main delivery conduit 3. The connection mechanism can be a threaded screw type connector or a friction locking mechanism. The secondary supply conduit may be preferably made from a breathable material that allows water vapour to pass through the supply conduit and into ambient air while substantially preventing liquid water or breathing gases to pass out of the supply conduit. The supply conduit may have regions of breathable material along its length or alternatively the entire conduit wall may be breathable. Materials may be breathable due to their composition, physical structure or a combination thereof. The mechanisms of water vapour transmission through these breathable materials are numerous and known in the art. The purpose of the breathable region or regions of the supply conduit wall is to allow passage of water vapour from the gases path along independent of specific drain locations. This reduces the build up of condensation within the breathing tube by drying the humidified breathing gases (by transmitting water vapour to the surrounding ambient air) during their flow through the breathing tube. An example of such a material is SYMPATEX™ or GORE-TEX™ or NAFION™ and so on.

The result of providing a short secondary supply conduit 62 is that a majority of humidity in the gases is transported to the patient, and there is an insignificant and negligible loss of humidity through the breathable wall of the short secondary supply conduit, while condensate forming is reduced.

The nasal cannula and its various features will now be described in more detail.

Nasal Cannula

The preferred form of the nasal cannula 30 which forms part of the patient interface 20 shall now be described in more detail with particular reference to FIGS. 4, 5, 6, 7, 8, 9 and 10.

The nasal cannula 30 of the preferred form comprises two main parts: a manifold portion 35 and a face mount part 32. The preferred embodiments of these two parts will now be described with particular reference to FIGS. 4 and 5.

Manifold Portion

In the preferred form, the manifold portion 35 is in use connected to and in fluid communication with the secondary supply conduit 62 as has been described above. However, it could be connected directly to the main delivery conduit 3 in alternative embodiments. Where the phrase 'gases inlet manifold part' is used in this specification, this should be taken to mean the manifold portion 35 in combination with the secondary supply conduit 62, or just the manifold portion 35, as appropriate.

Figure 4:
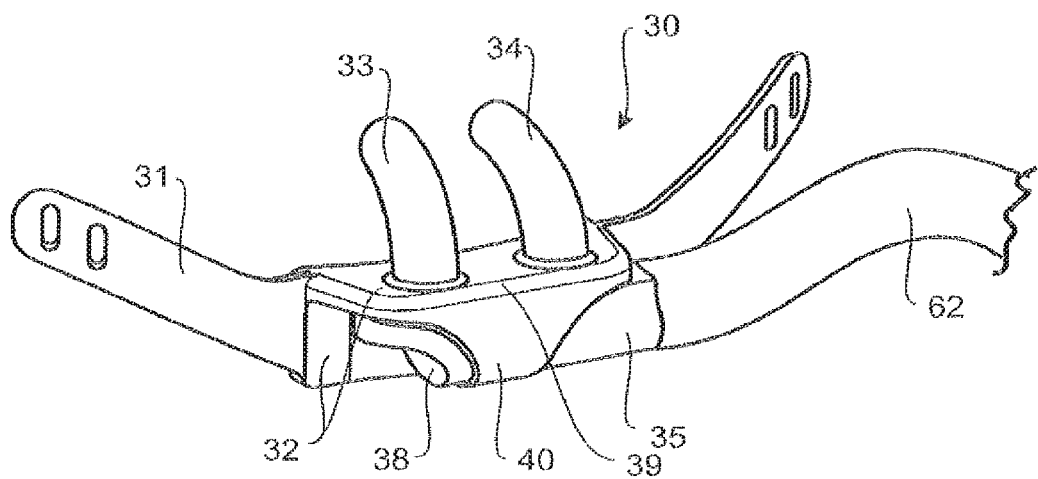
FIG. 4 shows a perspective view from the front and to one side of the most preferred form of nasal cannula, the nasal cannula of the preferred form having a face mount part and a manifold part, the manifold part removable from the face mount part, the secondary supply conduit connected to the manifold part.
Figure 5:
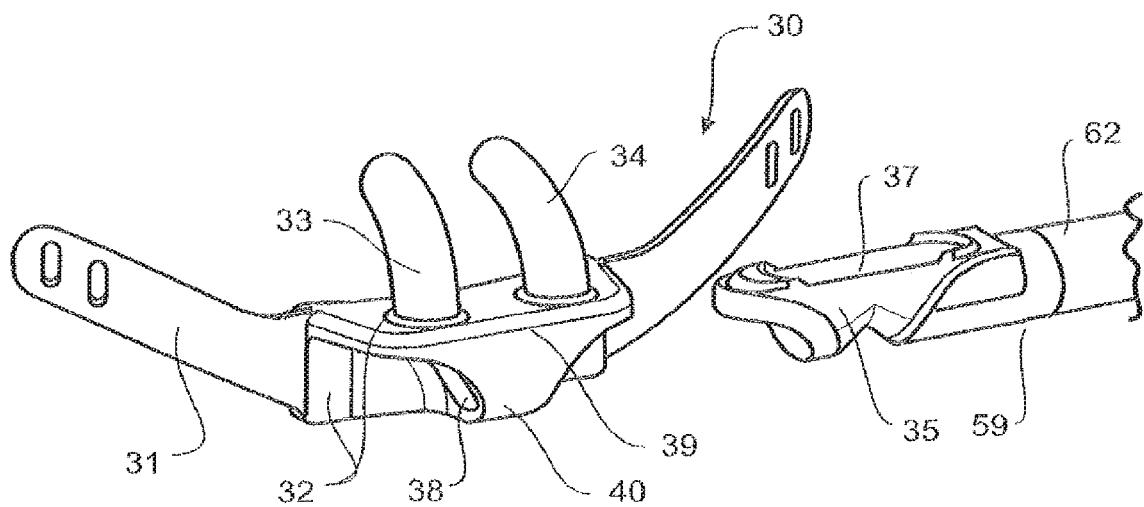
FIG. 5 shows the patient interface of FIG. 4 with the manifold part removed from the face mount part.

It should also be noted that the preferred form as shown in FIGS. 4 and 5 shows the manifold part 35 as being detachable from the remainder of the nasal cannula 30. However, the manifold part 35 could also be formed as an integral part of the nasal cannula 30 if preferred or required—that is, so that the manifold part 35 and the face mount part 32 (described below) are one item.

The preferred form of manifold part 35 is generally tubular in shape having a substantially circular inlet 59 on one side that curves to an elongated oval outlet 37, the outlet 37 being formed on one side of the manifold part 35 so that it is perpendicular to the inlet 59. The circular inlet 59 in the preferred form receives the patient end of the secondary supply conduit 62, such that the gases from the secondary supply conduit 62 can flow through the manifold part 35 (inlet 59 could alternatively be oval, or any other suitable shape—it does not have to be circular). In the preferred embodiment the manifold part 35 is integrated with the secondary supply conduit 62 (i.e. it is not intended to be removed and replaced repeatedly in use, although it can be removed if required), but alternatively the manifold part 35 could be removably attached to the secondary supply conduit 62. The manifold part 35 engages with the face mount part 32 so that gases can pass through the outlet 37 and transfer from the secondary supply conduit 62 to the patient 2 through the nasal prongs 33, 34 (described in detail below).

In the preferred embodiment the manifold part 35 is manufactured from a hard plastic material that only deforms under relatively high loading conditions (that is, it cannot easily be crushed in the hand of a user). The manifold part 35 may be moulded, injection moulded, machined or cast.

The manifold part 35 in use is connected to the face mount part 32, so that gases exiting the manifold part 35 enter the face mount part 32. The term "connected" in the context of this specification should be taken to mean either "detachable" or "integral with", as appropriate. The face mount part will now be described in detail.

Face Mount Part

The face mount part 32 includes the nasal prongs 33, 34, so gases passing through the face mount part 32 can enter the nasal prongs 33, 34 and be delivered to the patient 2. The preferred form of nasal prongs 33, 34 extend parallel to each other, curving upwards and inwards from the face mount portion 32. In the preferred embodiment, each nasal prong is equidistant from the centre of the face mount part. The structure of the prongs 33, 34 will be described in detail below.

The face mount part 32 of the preferred embodiment includes side straps 31 and an open tubular recess 38, integrally moulded together as shown in FIGS. 4 and 5. The open tubular recess 38 extends below the face mount part 32 and is adapted to receive the manifold part 35 (for the preferred embodiment where the face mount part 32 and the manifold part 35 are separable items). The face mount part 32 has a lip 39 that extends around the upper edge of the open tubular recess 38. The manifold 35 is connected to the face mount part 32 by a friction fit and the lip 39 on the face mount part 32 helps to grip the manifold part 35 and form a strong sealed connection between the manifold part 35 and the face mount part 32. The open tubular recess 38 is divided by a rib 40 which extends below the face mount part 32. The rib 40 helps to cradle and hold the manifold part 35 in the correct position as it engages with the face mount part 32, the rib 38 extending around the outside of the manifold part 35. Outlet 37 on the manifold part 35 aligns in use with the underside of the face mount 32 portion when the manifold part 35 is connected to the face mount part 32. This alignment minimises and reduces the amount of gases which leak out of the nasal cannula arrangement 30, allowing effective treatment of the user by delivering maximum amount of humidified gases.

The side straps 31 are used to attach the head strap 50 or the ear loops to the face mount part 32. The side straps 31 comprise a pair of straps (shown as straps 31 on the figures) which extend from either side of the face mount part 32, and which in the preferred embodiment are formed as an integral part of the face mount part 32. The headgear strap 50 is in use attached to the side straps 31 so that the patient interface can be worn by a user in use. In the preferred form the ends of the headgear strap 50 are looped through a pair of slits on the side straps 31, with the ends including velcro or similar to hold the ends in place when the y are looped back on themselves. Alternatively the headgear strap 50 or loops 66 may be clipped onto the side straps 31, for example by way of co-operating male-female clips, or adhesively attached to the side straps 31.

In the preferred embodiment the face mount part, nasal prongs, side straps and the open tubular recess are all manufactured as one continuous item. The face mount part 32, nasal prongs 33, 34, side straps 31 and the open tubular recess 38 are all manufactured out of flexible polymer material or silicone, preferably a soft thermoplastic elastomer (TPE).

The nasal prongs will now be described in more detail.

Nasal Prongs

The following is a description of the nasal prongs. In the following description the term "rear", or "back" or any such synonym refers to that part of the structure that faces towards and is closest to the patients face when the nasal cannula is in use. The term "front" or "forward" or any such synonym refers to the side, face or part which faces away from and is furthest away from the face of a user of patient in use. The term "top" or "upper" refers to the side, face or part that is pointing away from the floor, when a user or patient wearing the interface is standing or sitting upright and looking forward. The term "bottom" or "lower" refers to the side, face or part that is directed or pointing toward the ground, again when a user or patient wearing the interface is standing or sitting upright and looking forward.

Figure 6:
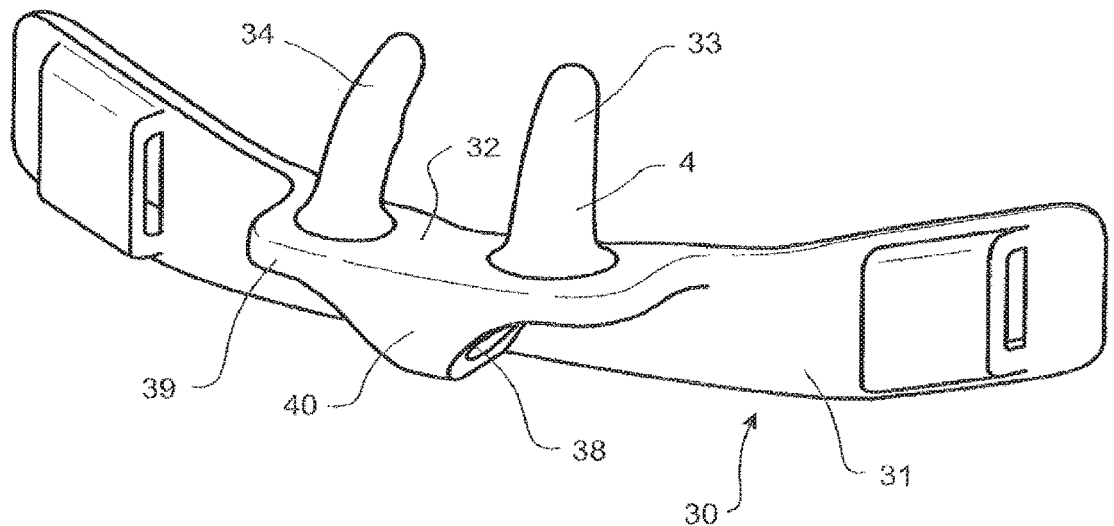
FIG. 6 shows a perspective view from the front and to one side of the preferred form of the face mount part of the preferred form of nasal cannula, the face mount part including a section adapted to receive the manifold part, and a pair of nasal prongs extending from the face mount part.
Figure 7:
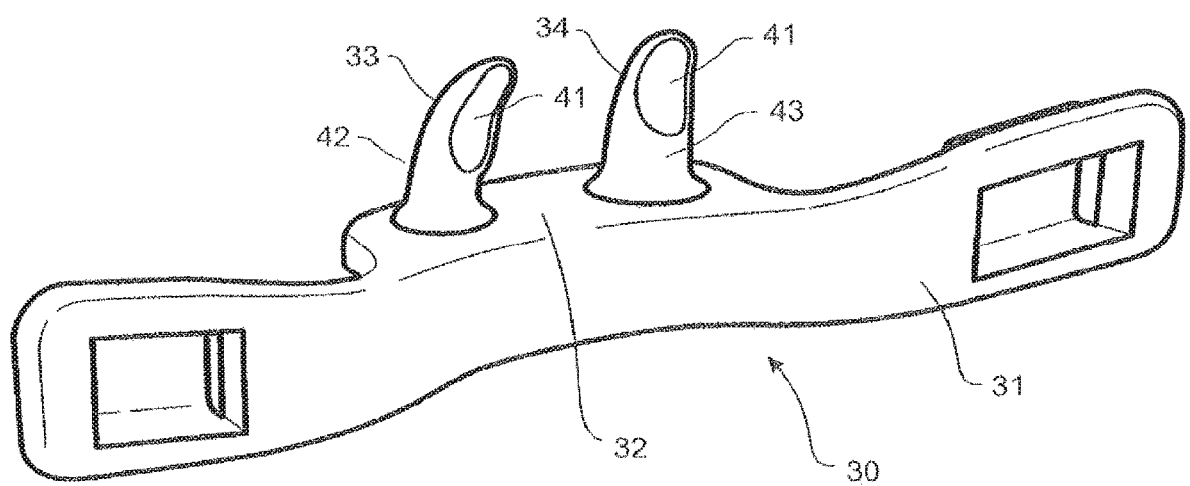
FIG. 7 shows a perspective view from the rear and to one side of the preferred form of the face mount part of the nasal cannula, the face mount part having a pair of nasal prongs extending from the face mount part, each of the nasal prongs having a gases exit cut-out on their rear face, at the upper part of the prong.
Figure 8:
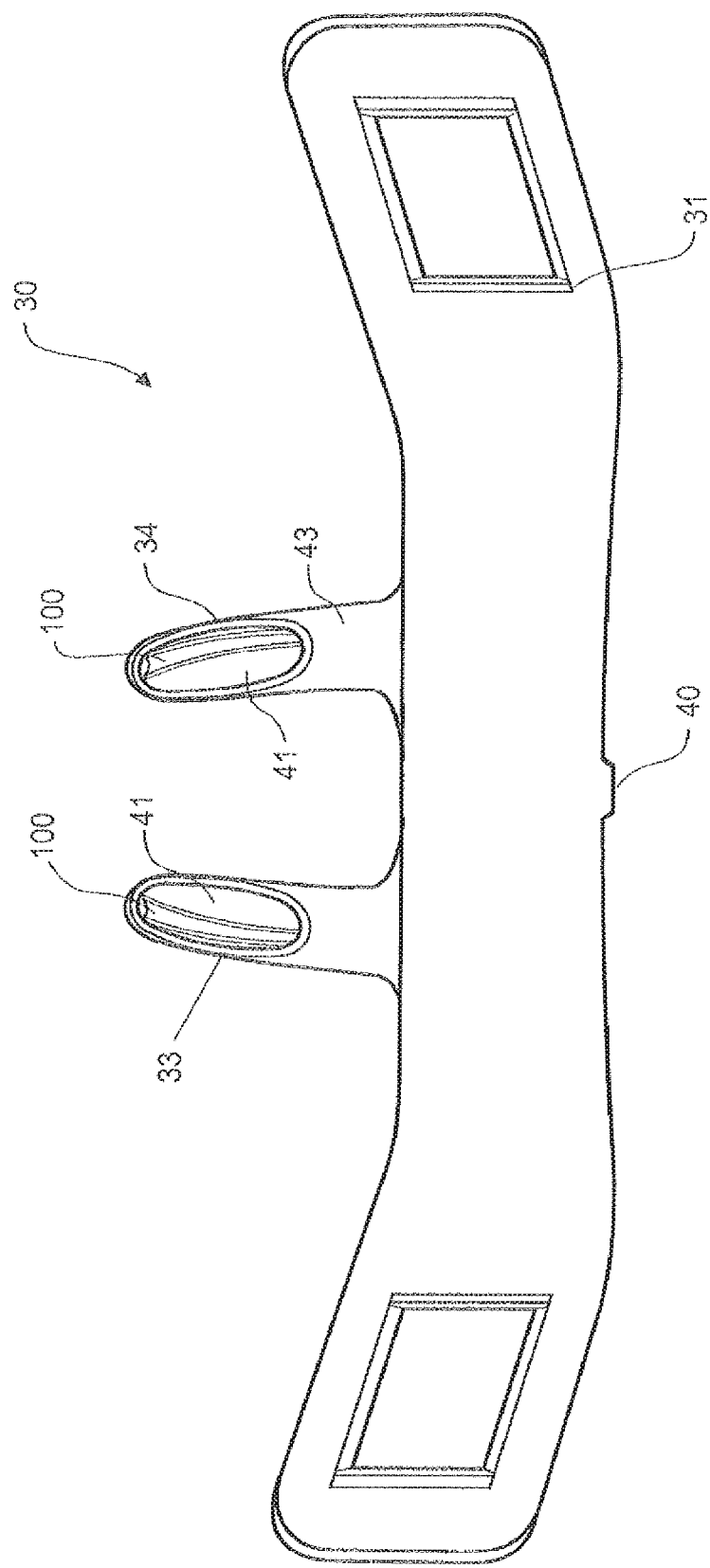
FIG. 8 shows a view directly from the rear of the manifold part of FIG. 6, with the gases exit cut-out clearly shown.

In the preferred embodiment the face mount part 32 includes two nasal prongs 33, 34 extending upwards and curving inwards from the upper surface of the face mount part 32 as shown in FIGS. 4, 5, 6 and 7. Referring to FIGS. 7 and 8, the nasal prongs 33, 34 extend from the upper surface of the face mount part 32 and each prong is placed in each nostril of the patient when the nasal cannula arrangement is in use. The prongs 33, 34 are configured to deliver gases to a patient. The prongs 33, 34 receive humidified gases from the delivery conduit 3 via the secondary supply conduit 62, the manifold part 35 and the face mount part 32. It should be noted that in the preferred embodiment, the gases inlet manifold part 35 receives the gases from the secondary supply conduit 62, with the gases passing through the gases inlet manifold part to the face mount part 32 and then into the nasal prongs 33, 34. The nasal prongs 33, 34 are therefore in fluid connection with the gases inlet manifold part 35 and receive the gases from the secondary supply conduit 62. As has already been outlined above, the gases inlet manifold part 35 and the face mount part 32 could be formed as one item—that is, as a combined manifold and face mount part, and this item could if required be formed to act as a manifold, with the prongs integrally formed with the manifold, the manifold attaching to one or more gas hoses or tubes, in a similar manner to typical nasal cannulae which are known in the prior art. Where the phrase 'gases inlet manifold part' is used in this specification, it should be taken as being broad enough to encompass this arrangement. The phrase should also be taken as being broad enough to be inclusive of dual hoses of the type known in the prior art that connect one to each side or end of the manifold tubing and which loop over the ears of a user before attaching to a main delivery conduit or a secondary supply conduit. It should also be noted that where the phrase "a gases inlet manifold part adapted to form a fluid connection with a delivery conduit" is used, this should be taken to mean that the gases inlet manifold part may be directly connected, or indirectly connected with intervening items included such as a secondary supply conduit, or dual hoses of the type known in the prior art (or both).

In the preferred embodiment the nasal prongs 33, 34 are generally tubular in shape, with an upwards and rearwards curve. The nasal prongs curve upwards and towards the back of the patient's head when in use. Preferably the prongs are curved toward the back of the patient's nasal passages, such that the stream of gases delivered by the prongs is directed toward the back of the patient's nasal passages. The curvature of the nasal prongs 33, 34 ensures the prongs follow the natural curve of a human's nasal passage. Preferably the prongs follow a curve of radius 10.5 mm but any radius between 5 and 20 mm is suitable, and larger or smaller sizes are also possible without departing from the scope of the invention. The curvature of the prongs 33, 34 ensures gases are delivered into the nasal cavity of the patient and this helps to reduce leakage of gases from the nasal cavity. The curvature of the prongs 33, 34 provides the advantages of added comfort and effective delivery of respiratory gases into a patient's nasal cavity.

In the preferred embodiment the nasal prongs 33, 34 fit into the patient's nasal passage. Preferably each of the nasal prongs are generally circular in cross section. Alternatively the nasal prongs may be triangular or oval in cross section. A circular cross-section is most advantageous for use since this shape conforms most closely to the shape of a human's nasal passage, thus providing a comfortable fit for the patient and ensuring the correct delivery of the therapy. However, the nostrils and nasal cavities of users are not perfectly circular or geometrically standard, and other cross-sections (such as the triangular or oval cross sections mentioned above) may be preferable.

Figure 9:
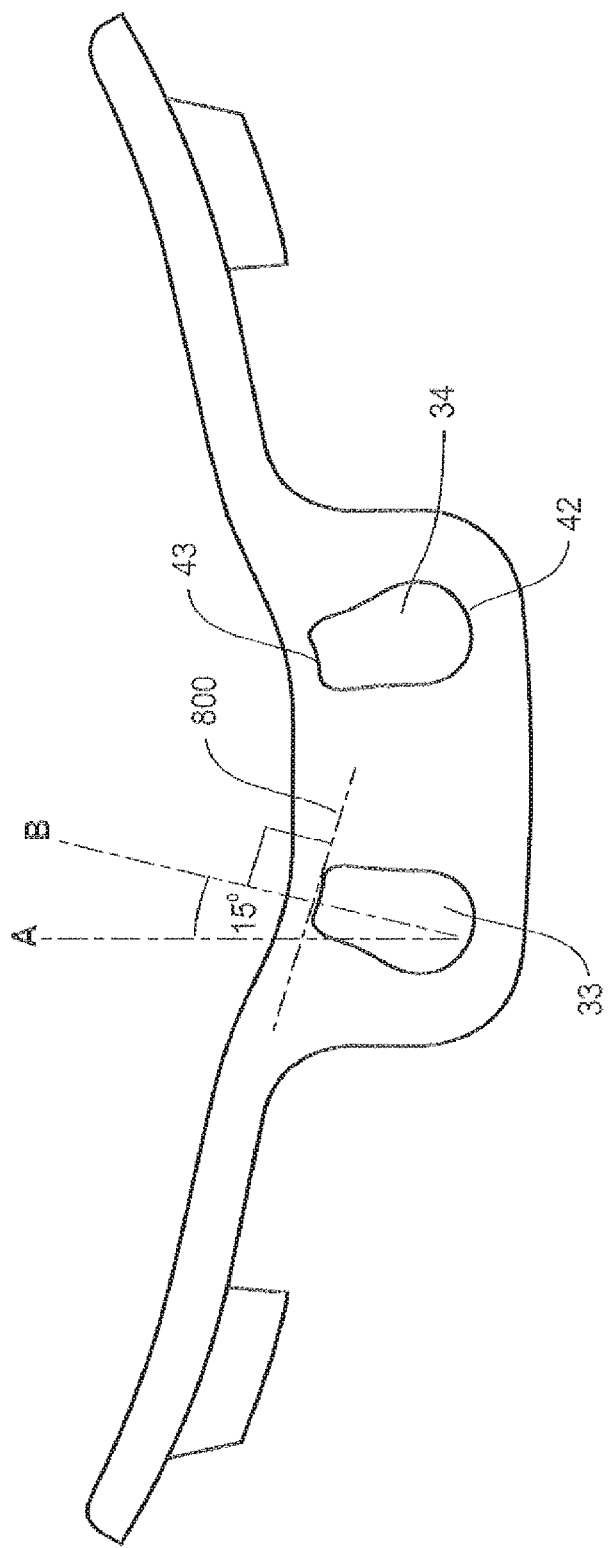
FIG. 9 shows a top view of the preferred form of face mount part of the preferred form of nasal cannula, the view showing the preferred inwards angle of the nasal prongs relative to a vertical plane which bisects the face mount part, and the preferred alignment of a surface which defines the perimeter of the cut-out section in the preferred form.

In the most preferred form the nasal prongs are arranged equidistant from the centre of the face mount part. Preferably the nasal prongs are angled to face slightly inward towards one another as best shown by FIG. 9. When viewed from the top, the centre of each of the nasal prongs is preferably angled 15 degrees inward from the vertical line A as seen on FIG. 9. That is, the angle X between line A and line B, as shown on FIG. 9, is 15 degrees. This applies to both of the pair. The line A defines a vertical plane, which is substantially parallel to the vertical plane of symmetry which bisects the face mount part 32 of the nasal cannula 30—that is, a line or plane which would bisect the human nose when the nasal cannula is positioned on the face of a user. The prongs 33, 34 are angled inward towards one another at 15 degrees to provide the most comfortable fit when in use. It has been found that having the nasal prongs angled inwards at 15 degrees provides the most comfortable fit or position for a user and an optimal position for delivering therapeutic gases to a patient. The nasal prongs may be placed at any other angle larger or smaller than 15 degrees. The range of angles between line A and line B could for example be between 0 degrees to 60 degrees of inward angle. Alternatively the nasal prongs could be angled outward from the vertical line A. Angling the nasal prongs outward is not preferred because angling the prongs outwards means the prongs may not follow the natural shape of the nasal passage potentially making the prongs uncomfortable to use for most users. However, this may be suitable in some situations, or for some users in certain circumstances.

Figure 10:
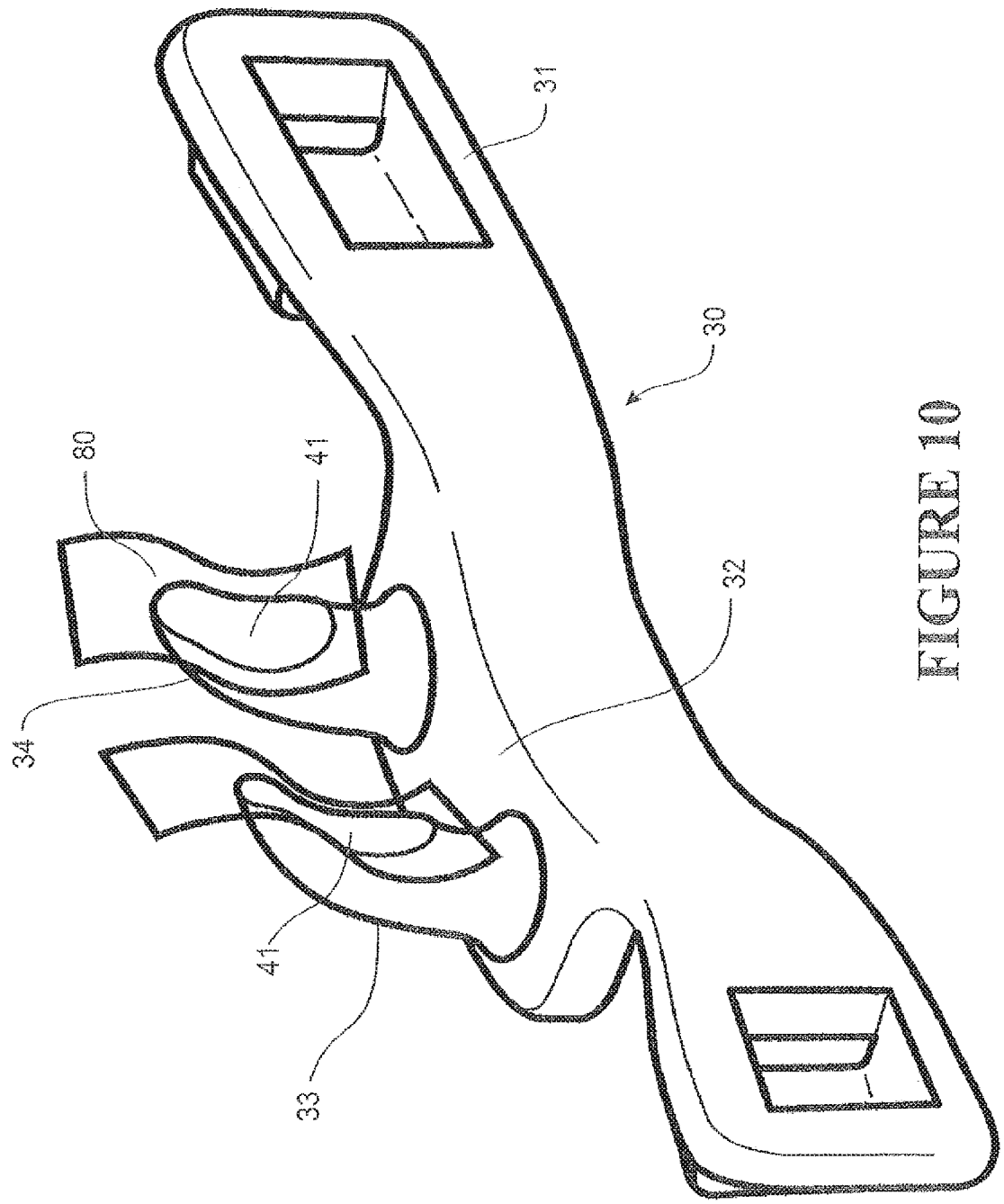
FIG. 10 shows a rear perspective view of the nasal cannula of the preferred embodiment, the view showing the preferred form and placement of the surface.
Figure 11:
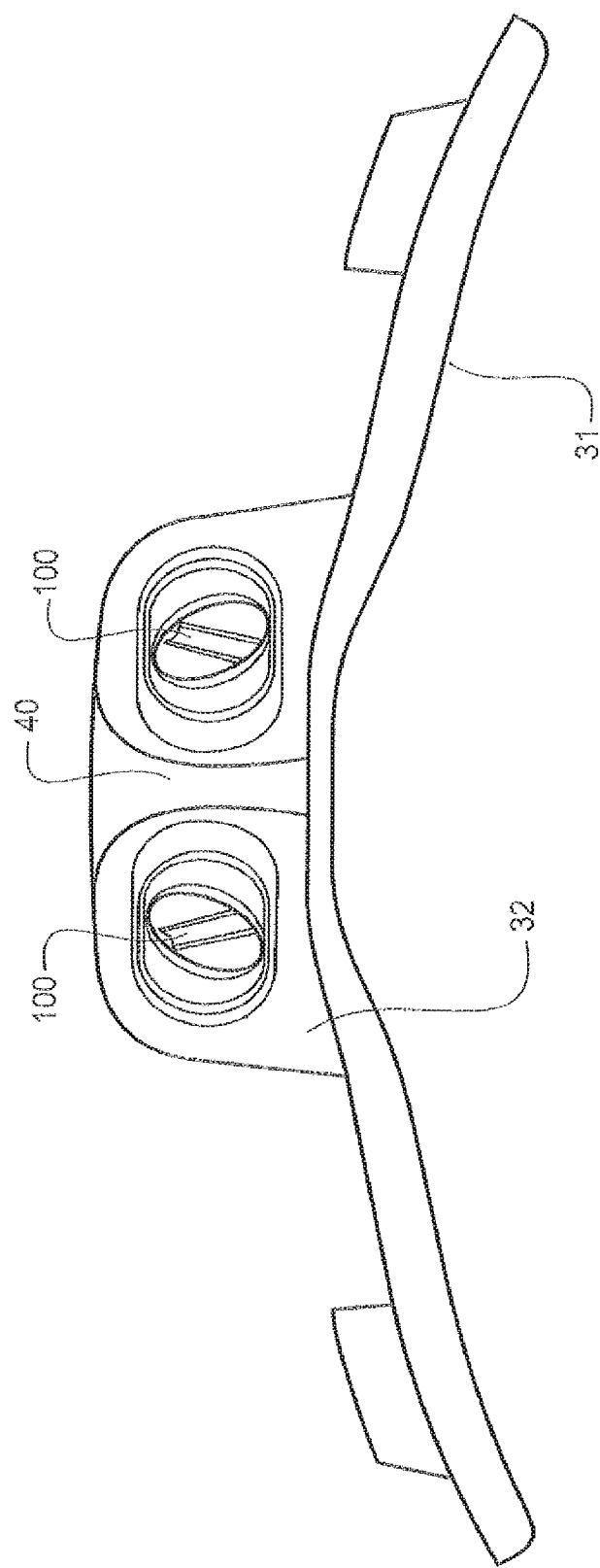
FIG. 11 shows a view from under the nasal cannula of the preferred embodiment
Figure 13:
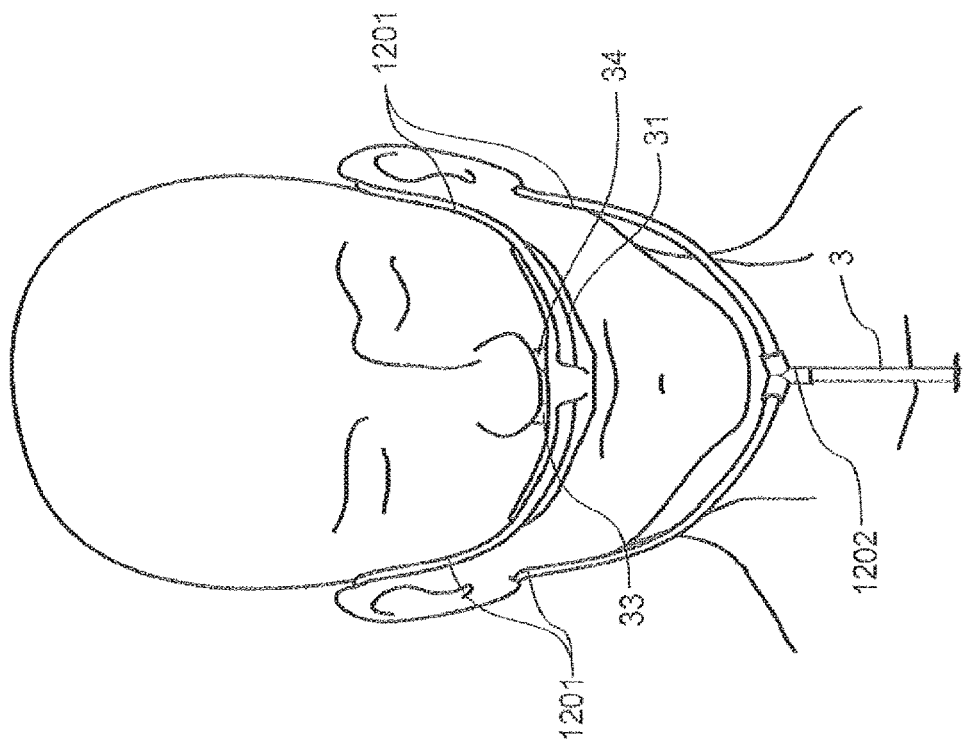
FIG. 13 shows a further alternative embodiment of the nasal cannula where the carrier tubes extend from the manifold, the carrier tubes connect to the face mount part and the prongs extending from the face mount part
Figure 12:
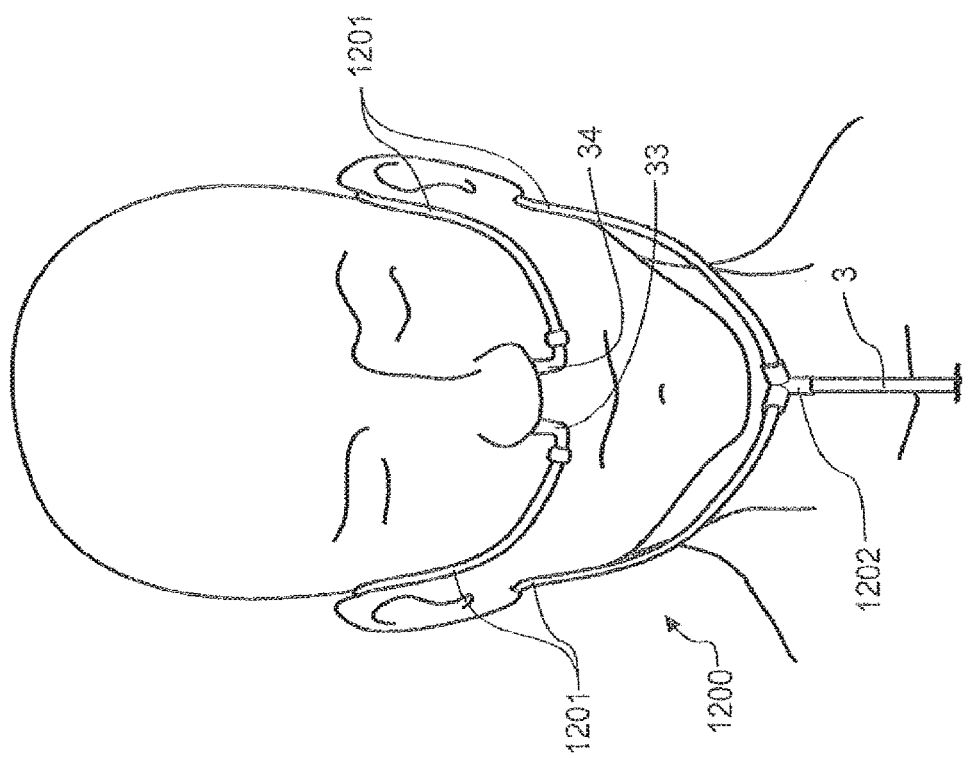
FIG. 12 shows an alternate embodiment of the nasal cannula, the cannula includes a manifold with two carrier tubes extending from the manifold and looping around the user's ears and a prong connected to the end of each carrier tube.

Each of the nasal prongs includes a gases exit cut-out section 41 on the rear side 43 of the nasal prong, as shown in FIGS. 7 and 8 and 10. The gases exit cut-out or cut-out section in the preferred embodiment gives each of the prongs the appearance of a scoop. The front side 42 of the nasal prong (the side further away from the patient) extends further upwards and inwards from the face mount part 32, and forms a guide wall that guides humidified gases into the patient's nasal passage when the nasal prongs 33, 34 are in use. The gases exit cut-out in the prong has a sectional area greater than the cross-sectional area of the prong at or close to the point of entry of gases into the prong from the manifold section—that is, the cross-sectional area of the prong is greater at the point where the gases exit the prong (and enter the users nare), in comparison to a point at or close to where the gases enter the prong from the manifold section.

The cut-out section 41 can be formed in various shapes. In the preferred embodiment the cut-out section 41 is oval in shape when viewed from the rear, as best seen in FIG. 8. That is, when viewed from the rear, the perimeter of the cut-out section 41 describes an oval shape, the top of the oval angled slightly inwards towards the other nasal prong. The cut-out section could also be triangular (with one point of the triangle oriented towards the base of the prong, and the other two corners at the topmost inner edges of the cut-out section 41). The cut-out could also be rectangular in shape.

The cut-out can extend from various positions along the nasal prong. Preferably the cut-out section 41 extends from between halfway and two thirds of the way along the nasal prong, when measured from the top tip of the nasal prong. Alternatively the cut-out section 41 may extend from less than halfway along the nasal prong, when measured from the top tip of the nasal prong. As a further alternative the cut-out may extend the entire length of the prong. In the most preferred embodiment, the cut-out section 41 extends from between halfway and two-thirds of the way along the nasal prong to provide the best advantages. It has been found that having the cut-out extending between halfway and two thirds ensures the optimal size of the opening. Placing the cut-out at this position ensures the most optimal size of cut-out to provide the advantages described later in this specification. For nasal prongs according to the preferred embodiment, this corresponds to a cut-out having a height of 3 mm to 15 mm. However, the size of the cut-out could fall outside this range if required for alternative forms.

In the preferred embodiment the cut out 41 is formed during the moulding process. It is preferred that the prongs are moulded by injection moulding, casting or vacuum forming. The mould used to produce the desired prong shape has the cut-out feature built into it.

In alternative embodiments the cut-out section 41 is created by cutting across the rear 43 of each of the prongs 33, 34 after these have been formed in an initial forming operation—e.g. after the face mount part 32 has been moulded in an initial forming operation, the cut-out is formed by removing material either by machining or by hand.

The reverse S-shaped surface 80 which defines the cut-out section is best shown in FIG. 10. The bottom edge of the surface 80 is shown in FIG. 9 as line 800. As can be seen, for each prong, line 800 is perpendicular to a line through the centre of the nasal prong, and is aligned with the rear edge of the prong. This is best shown in FIG. 9. Preferably the surface 80 is shaped as a reverse S shape as shown in FIG. 10. The surface 80 extends a certain distance inward to form the preferred 'scoop' shape of the gases exit cut-out. The reverse S shape is aligned substantially vertically. The reverse S shaped surface produces the most preferred size and shaped cut-out. After forming, the edges or perimeter of the cut-out section 41 conforms to the surface of the reverse S-shaped surface, as shown in FIG. 10. Such a surface results in the optimal cut-out shape that provides the advantages described below.

In the preferred embodiment the rear wall 43 of the nasal prongs 33, 34 also includes a reinforcing feature (not shown in the figures) that extends upward along the length of the rear wall of the nasal prong. The reinforcing feature helps to maintains the rear wall 43 of the nasal prong in an upright position. Preferably the reinforcing feature is formed as a ridge running at least part of the way along the rear face 43 of the nasal prongs 33, 34. This ridge can be on either the inside or the outside of the rear wall 43, as the rear wall does not in use generally contact the upper lip or nares of a user, and the reinforcing feature will therefore tend not to interfere with the face of the user and make than uncomfortable. Preferred and alternative forms of reinforcing feature will be described in greater detail below.

Due to the curvature and shape of the nasal prongs 33, 34, the stream of air will tend to flow along the front wall of the prongs 33, 34, rather than the rear wall 43—the air stream flows along the outside of the bend rather than the inside.

Advantages

The cut-out sections within each nasal prong provide a number of advantages. The main advantages are as follows:
1) Each of the prongs can deform or misshape more easily, as they have less structural rigidity (a piece of their support structure is missing, so they can deform more easily), and are therefore more comfortable in a patient's nasal passage, 2) The gases do not exit from the prong as a jet, through a small aperture. The cut-out provides a larger area of exit aperture at the exit of the prongs, so that the velocity or air speed of the gases is reduced at the point where they exit the prong(s). That is, the size of the exit aperture (defined by the edge or perimeter of the cut-out section) is greater than the size or cross-sectional area of the inlet aperture, which is defined by the base of the prong where it is connected to the face mount part 32. The air speed of the gases reduces as the area increases. That is, each prong is shaped so that the velocity of gases exiting said prong is reduced in comparison to the velocity of gases at or close to the gases point of entry to the prong. This allows a proportionally greater volume of gases to be delivered to a patient without causing discomfort (in comparison to a cannula prong which does not include a cut-out). With the cut-out cannula, air jetting effects are reduced. The jetting of the airflow is reduced based on the continuity equation for energy or mass conservation, which states that increasing the cross sectional area equates to a reduction in the velocity of the airflow. A jet of gas delivered into a user's nasal passage can irritate or potentially damage the tissue within the nasal passage. A reduction in the velocity of the flow of gases as delivered by the nasal prongs reduces irritation in the user's nostrils and thus the jetting effects. It also follows from the continuity equation that the larger the aperture a gas is flowing through, the larger the amount of diffusion. 3) The stream of gases is directed in a generally rearwards direction (relative to the head of a user) relative to the nasal passage of a user.

These advantages are discussed in more detail below.

The nasal cannula arrangement 30 as shown in FIGS. 6 and 7 is suitable for the delivery of high airflow, high humidity gas flow to the patient's nasal cavity. In the preferred embodiment, the cut-out extends between from the top of the prong to between half and two thirds of the distance to provide the largest cut-out. Further, the shape of the cut-out (reverse S-shape surface as described above) contributes to ensuring maximum diffusion and reduction of air jetting effects.

In prior art cannulas, the cannula prongs will generally have an exit aperture which is substantially the same size as their inlet aperture (e.g. where the base of the prong is connected to a manifold). In the cannula of the present invention described above, the size and shape of the cut-out helps to reduce the air speed at the point of exit from the prong, and to direct the gases in a generally rearwards direction. It has been found that this helps to increase user comfort and compliance with a therapy regime to a surprising degree. Furthermore, the decreased velocity flow of respiratory gases from the cut-out 41 of the nasal prongs 33, 34 helps to ensure that the user will breathe as normally as possible.

The reduction in air velocity due to the cut-outs in the prongs 33, 34 allows the use of a higher flow rate than is generally the case in the prior art. In therapy, high flow rates are preferred in order to meet the patients requirements. Using high flow rate ensures that where possible, the entire volume of an inhaled breath comprises respiratory gases. However, due to increased patient discomfort and potentially dangerous side-effects with higher flow rates, a trade-off is normally made between patient comfort/safety, and flow rate. Lower flow rates than may be optimal are used to ensure the patient is comfortable enough to conform with a therapy regime. Using these lower flow rate means at least part of, and generally a majority of, the user's breath is composed of ambient air which can be detrimental to the therapy provided by medical gases. Using relatively higher flow rates and having nasal prongs that allow humidified medical gases to be delivered at high flow rates is advantageous. This helps to ensure that the most efficient and effective therapy provided to a patient. Surprisingly, it has been found that by using the prongs as described above—i.e. prongs that include a cut-out section—flow rates between (but not limited to) just above 0 L/min to 80 L./min can be delivered to a user and initial user feedback suggests that there is decreased discomfort and a greater tendency towards regime compliance. The prongs can be re-sized—e.g. for use in neonatal applications—without departing from the scope of the invention, with the flow rates or flow range being considerably lower in neonatal applications. It is anticipated that flow rates of up to 120 L/min could be used in certain circumstances. However, it is anticipated that the preferred range will be in the order of 20-50 L/min for adults, 5-30 L/min for Paediatric patients, and just over 0 L/min to 8 L/min for Neonatal patients. The cut-out design is effective at low flow rates when used on neonatal patients (as small as 400 gms), where flow rates of 1-8 L/min would otherwise create very high velocities due to the small size of the cannula and patient.

The cut-out sections 41 in the nasal prongs 33, 34 causes the nasal prongs 33, 34 to be more deformable than prior art nasal prongs which do not include cut-outs. Surprisingly, it has been found that the addition of cut-outs does not significantly negatively impact on the gases delivery efficiency, and as well as the advantages outlined above, allows the nasal prongs 33, 34 to be bent and flexed to a greater extent than prior art cannula prongs, to fit comfortably into a patient's nasal passage. A range of sizes of cannulae will normally be used, to ensure a fitment range for all users. However, within each 'bracket' or range, the greater bending or flexibility helps improve user comfort. The cut-out 41 causes the nasal prongs 33, 34 to be more flexible than completely "tubular" or round shaped nasal prongs. Generally in use the nasal prongs rest against the nasal mucosa. In other nasal cannula arrangements the nasal prongs exert a force on the nasal mucosa and this pressure can irritate the user, making wearing nasal prongs uncomfortable. This may even result in damage to the delicate nasal tissue. The gases exit cut-outs 41 within the nasal prongs allow the prongs 33, 34 a greater degree of flexibility within the nasal passage, as the prong pushes against the nasal mucosa tissue. The flexing of the prongs reduces the pressure exerted on the nasal mucosa making it more comfortable and potentially safer for the user to wear.

The cut out sections 41 within the cannula are also advantageous because they have made manufacturing of the cannulas quicker. The cut out sections 41 allow the cannula to be easily lifted off the forming tool by a robot or human operator. The cut-out sections 41 have halved the cycle time.

Reinforcing Feature

Preferably the nasal prongs each include a reinforcing feature 100 running along the inner surface of the front wall of the nasal prong helps the nasal prong to return to its original shape after bending and flexing. This is shown in FIG. 8. Preferably the feature provides strengthening for the nasal prong against a compressive or tensile force or both acting on the nasal prong. The feature effectively forms a reinforcing spine along the inside surface of the front wall 42 of the prong, with the feature extending upward from the base of the prong and following the contour of the prong. The reinforcing feature 100 acts to allow lateral and rotational movement of the prong and allows the nasal prong to elastically deform in compressive and tensile force directions and exerts a restorative force to ensure the prong returns to its original shape. In one embodiment, the reinforcing feature 100 is an upward extending bead running from the base of the prong to the top of the prong. In the most preferred form the rib is located along the inner surface of the front wall 42. The bead extends upward from the base of the prong to the top of the prong. Preferably the bead extends the entire length of the prong and follows the contour of the prong. Alternatively the bead may only extend a partial height of the prong. Alternatively the bead may be located on the outer surface of the front wall. In a further alternative form the bead may be located along the back wall, either on the inner or outer surface of the back wall. The bead is preferably over moulded onto the prong. The reinforcing feature (in this form the bead) is preferably formed from a more rigid material than the prongs. The bead is applied to the prong by a co-injection process. The co-injection process involves injection moulding the prong from one material, transferring the prong and/or manifold and face mount part to another tool where the bead material is injection moulded over the prong. The bead acts like a spine to support the prong.

In another form the reinforcing feature 100 may be a rib that extends upward from the base of the prong, along the height of the prong and follows the contour of the prong. The rib is preferably located on the inside surface of the front wall 42 but may be located on the outer surface of the front wall 42. Alternatively the rib may be located on the back wall 43. The rib may be located either on the inner surface or outer surface of the back wall 43. The prong preferably includes a plurality of ribs formed along the inner surface of the front wall. The ribs preferably extend the entire distance of the prong, but may alternatively only extend a partial distance. The ribs are preferably identical to each other in dimensions. The ribs are preferably equally spaced apart along the prong. The ribs form a skeletal structure that supports the prong and reduces deformation of the prongs. The ribs are preferably formed from a co-injection moulding process as described for the bead. The ribs are preferably made of a material that is more rigid than the material used to make the prongs.

The prong may also include a series of ribs (not shown) running generally horizontally across the prong. The ribs maybe used in combination with the reinforcing feature (e.g. the bead) to strengthen the nasal prongs in compressive and tensile directions, while allowing lateral and rotational movement. Preferably the reinforcing feature, (with or without ribs) is present on the front wall 42 of nasal prong. This is advantageous since this provides the greatest strengthening and also because the material used for the prongs responds best in compression. Preferably the reinforcing feature is formed integrally with the nasal prongs during the forming process. Alternatively, a reinforcing feature can be attached to the nasal prongs after forming—e.g. by gluing or ultrasonic welding. Preferably the feature is made from the same material as the nasal prong. Alternatively the feature or the ribs could be made from a stiff material such as another polymer material.

The reinforcing feature could alternatively be created by having the front wall 42 thicker than the backwall 43, when viewed from above. The increased thickness of the front wall 42 effectively provides lateral and rotational movement of the prong while providing improved strength characteristics under compressive and tensile loads. The thicker front wall 42 ensures that the nasal prongs 33, 34 do not collapse or tear when subjected to compressive or tensile forces.

A potential problem with "tubular" or "round" nasal prongs of the prior art type is the possibility of creating a seal in the patient's nasal passage. Although a seal is desirable in certain circumstances if using e.g. nasal pillows of the type described in WO 2008/014543, in other circumstances, a seal within the patient's respiratory system can lead to an overpressure being created within the patient's nares. This overpressure can lead to barrotrauma resulting in severe injury and possible patient death. It can also interfere with the patients natural breathing or self-breathing. The additional flexibility and greater aperture size provided to the nasal prongs 33, 34 by the cut-outs 41 aids in minimizing the risk of the cannula creating a seal in the patient's nares. However, it should be noted that a seal is sometimes desirable, and although in the preferred embodiment, a nasal cannula arrangement which is not intended to seal has been described, the nasal prongs 33, 34, or the face mount part 32, or both, could be adapted to seal against the nostrils of a user. However, this is not the preferred form.

The flexibility of the side straps 31 allows for easy securement of the nasal cannula arrangement 30 on the user's face since the straps can easily be bent and flexed to fit around a user's face. The flexibility of the open tubular recess 38 in the preferred embodiment enables the open tubular recess 38 to fit around the manifold part 35 and create a secure friction fit or snap on fit. The face mount 32 part is moulded as a single piece of flexible plastic, silicone or rubber material for reliability and ease of use.

The nasal cannula arrangement and the nasal prongs in particular, as shown in FIGS. 2 to 10 are predominantly useful for delivering gases with high humidity and high flow rate which is advantageous to the patient.

Second Embodiment

A second embodiment the patient interface can also be used as part of the humidification system as described above in relation to FIG. 1.

The second embodiment of the patient interface broadly consists of a head securement mechanism substantially similar to that described above for the first embodiment, and a nasal cannula arrangement. The head securement mechanism is used to attach the patient interface to a patient's face and maintain the position of the patient interface in the correct position when in use. The head securement mechanism as described in relation to FIGS. 2 and 3 can also be used with the second embodiment of the nasal cannula. Alternatively no separate head securement mechanism needs to be used with the nasal interface. This alternative form of head securement will be described later. The humidification system with which the alternative nasal cannula arrangement is used can include a secondary supply conduit 62 similar to that described above, which allows gaseous or fluidic communication between the outlet end of the main delivery conduit 3 and the main part of the nasal cannula arrangement. However, in this alternative form, the secondary supply conduit 62 and the main delivery conduit 3 can be thought of as a single 'delivery conduit' in this context.

Nasal Cannula—Second Embodiment

The nasal cannula of the second embodiment will now be described in more detail. The nasal cannula of the second embodiment comprises 3 main parts: a pair of carrier tubes, a manifold section, and a pair of nasal prongs, one each of the pair of nasal prongs attached to each of the carrier tubes, the carrier tubes connected to the manifold section, which is connected to the delivery conduit as outlined above so that a stream of gases is delivered to the manifold section. The carrier tubes are used instead of the secondary conduit. The manifold section is formed as a Y-piece connector or a T-piece connector. The carrier tubes are connected to the branches of the Y-piece or T-piece manifold section, preferably with a friction fit. Alternatively the carrier tubes may be connected to the Y- or T-piece by threading or gluing. An even further alternative is the carrier tubes are formed integral to the Y- or T-piece. The Y-piece connector directs flow of gases from the secondary supply conduit to each of the carrier tubes. Preferably the Y- or T-piece is made of a rigid polymer material, the material rigid enough that it does not readily deform under common operational loads.

The carrier tubes can be attached to a head securement, or they can themselves be adapted to be used as a head securement mechanism. The carrier tubes are wrapped around behind the ears. The carrier tubes allow flexibility for head securement. The carrier tubes are light enough to wrap around a patient's ears and be comfortable for the patient to use. The use of carrier tubes makes the entire nasal cannula light in weight. This can help to increase the comfort level for a patient while using the nasal cannula. The carrier tubes also let people of various sizes to use the nasal cannula arrangement as long as the carrier tubes are long enough to be placed over their ears. The carrier tubes connect to the manifold and form a fluid connection with the manifold. The carrier tubes supply breathing gases to the manifold. The manifold has at least one prong extending from it, the prong delivering breathing gases from the manifold to the patient's nasal passage.

In an alternate form a nasal prong is attached to each of the carrier tubes at the patient end. The nasal prongs can be detachable from the carrier tubes. Preferably the nasal prongs are attached to the carrier tubes by a friction fit. Alternatively the nasal prongs are threaded into the carrier tubes. Another alternative is the nasal prongs are glued or attached to the carrier tubes by an industrial adhesive. As a further alternative the nasal prongs may be integrally formed with the carrier tubes.

In this alternative form, the prongs are substantially the same as prongs 33, 34 described above for the preferred or first embodiment. Each prong includes a cut-out on the rear side (that part closest to the face of a user in use), which in the preferred form is cut out of the rear of each of the prongs so that the edges of the cut-out conform to the surface of a reverse S-shaped surface.

Features of the Manifold and Prongs

The nasal cannula of the present invention can be used in high flow, high pressure therapy. A stream of gases enters the manifold substantially horizontally because the cannula has a side entry manifold. The stream of gases flows from the manifold into the prongs, out of the top of the prongs and into a user's nostrils. The inlet stream of gases enters the manifold in a substantially horizontal direction that is approximately orthogonal to the prongs. The inlet stream of gases turns through approximately ninety degrees as the gases flow into and up the prongs such that the stream of gases flows substantially aligned with the prongs axis of extension relative to the manifold. In prior art nasal cannula a substantial amount of the gases generally changes direction or turns at the entry of the prongs, which is a small area at the base of the prongs. The turning of the stream of gases within the entry to the prong causes the velocity of the gases stream to reduce. The reduction in flow velocity causes a pressure drop across the entry of the prongs since the pressure of the gases stream is proportionally related to the velocity of the gases stream. In prior art cannula approximately 65% of the gases stream is turned within the entry of the prongs. The pressure drop is proportional to the radius of the prongs to the power of four. The pressure and velocity drop is undesirable because it reduces the effectiveness of the therapy being delivered to the patient. The reduced pressure and velocity may also be dangerous for the patient as the patient may not be getting enough breathing gases. In CPAP type treatment the airways of the patient need to be consistently pressurised in order to allow the patient to breathe properly. A reduction in gases stream pressure due to the pressure drop across the entry to the prongs can cause the airways of the patient to collapse due to lack of pressure being supplied to the patient. The reduction in pressure can also cause the blower speed and power to increase in order to compensate for the pressure drop. This can be dangerous because the blower may be operating at high speeds. The pressure and velocity drop can also be adverse to patients receiving ventilator therapy because these patients will not receive adequate breathing pressure and the ventilator can begin to operate outside normal operating levels to try and compensate for the pressure and velocity drop. The prior art cannula may suffer from a pressure drop of approximately 25 cm $H_2O$.

Figure 14:
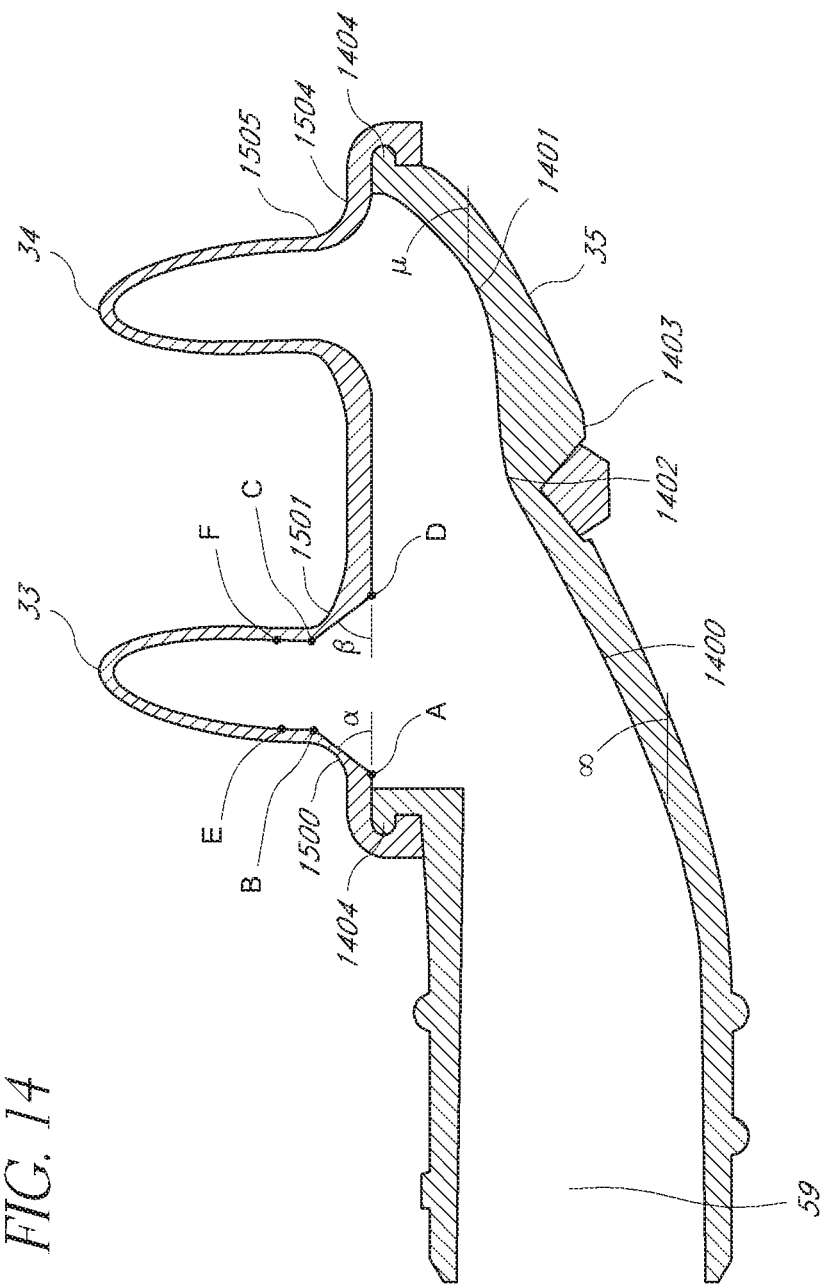
FIG. 14 shows a cross section view of the prongs and manifold, the manifold being engaged with the prongs, the figure also showing the transition sections and points to measure the rise and run of the transition sections.

The prongs and manifold of the present invention are shaped and adapted to turn at least part of the stream of gases inside the manifold rather than inside the prongs. FIG. 14 shows details of the prong and manifold features. The manifold of the present invention is shaped to deflect the stream of gases flowing into the manifold upward in substantially toward the prong. The manifold includes a manifold chamber defined by the walls of the manifold. The manifold wall 1400 opposite the upstream prong is angled upward relative the horizontal. The upward angle is labelled ∞. on FIG. 14. Angle .infin. is measured relative to the horizontal. Angle ∞ is at least 15 degrees upward from the horizontal. Most preferably angle ∞ is 22 degrees to the horizontal. Angle ∞ can be angled upward up to 45 degrees. The manifold includes a scalloped shape 1402 that creates a tooth 1404. The tooth 1404 allows the manifold 35 to engage with the face mount part 32 and the rib 40. The scalloped shape creates a second wall 1403 that is substantially opposite the downstream prong. The second wall is also angled upward from the horizontal at angle a as shown in FIG. 14. Angle μ is at least 30 degrees upward from the horizontal. Most preferably angle μ 33 degrees upward from the horizontal. Angle μ can be up to 90 degrees upward from the horizontal.

The prongs 33 and 34 each include transition sections on them. The transition sections are contours of the prongs that transition gradually from a substantially horizontal to a substantially upward orientation as shown in FIG. 14. Each prong includes an upstream transition section 1500 and a downstream transition section 1501. Each transition section 1500, 1501 connecting the horizontally oriented manifold 35 with the upwardly oriented prong 33, 34. The transition sections 1500, 1501 are preferably curved sections. Alternatively the transition sections 1500, 1501 may be straight sections or chamfers that connect the horizontally oriented manifold with the upwardly oriented prong. Preferably the upstream transition section 1500 has a shallower curve than the downstream transition section 1501. In the alternate form where the transition sections 1500, 1501 are straight line section, the downstream transition section 1501 is at a steeper angle than the upstream transition section 1500. In a further alternative form the transition sections 1500, 1501 may consist of multiple straight line sections. The downstream transition section 1501 comprises of straight line sections that are steeper than the upstream transition section 1500.

The transition sections 1500, 1501 change from a horizontal orientation to a vertical orientation within an area, meaning the section 1500 and 1501 transition from a horizontal to a vertical within an area. The area of transition is defined by vertical rise and a horizontal run. The rise and run are measured from specific points on the prongs. Preferably the run is the horizontal distance between a tangent point to the horizontal manifold and the narrowest point of the prong. Fox the upstream transition section 1500 the tangent point of the horizontal manifold is shown as point A and the narrowest point of the prong is shown as point B, in FIG. 14. Point B is the narrowest point of the prong because the prong extends in three dimensions. The prong extends upward and toward the patient. The narrowest point of the prong is point B due to the curved profile of the prong. Alternatively the horizontal run may be the distance between the point where the prong begins to transition from the horizontal and the narrowest point of the prong. In a further alternative the horizontal run may be the horizontal distance between a point tangent to the horizontal manifold (point A) and the point tangent to the prong when the prong is substantially vertical. The point tangent to the prong when the prong is substantially vertical is point E as shown in FIG. 14. The prong being substantially vertical as referred to earlier is in context of FIG. 14 only, relative to the prongs when viewed from the back of the prongs. In reality the prongs extend upward and backward, but FIG. 14 shows a cross section view of the prongs and manifold assembly. Vertical as referred to in the specification, with reference to point D is in context of the prongs as viewed in FIG. 14. The vertical rise is preferably the vertical distance between points A and B. In an alternate form the vertical rise may be calculated as the vertical distance between points A and E.

For the downstream transition section the horizontal run is also preferably measured from a point that is tangential to the horizontal manifold 35 to the narrowest of the prong. Point D on FIG. 14 is a point tangent to the horizontal manifold for the downstream transition section 1501. Point C is the narrowest point of the prong on the downstream transition section 1501. Alternatively the run for the downstream transitional section may be measured to the point where the prong is substantially vertical, point F in FIG. 14. In reality the prong is angled toward the patient and the prong curves. FIG. 14 shows a cross section and shows the prong as being substantially vertical in cross section. Point F is the point where the prong becomes substantially vertical in cross section. Point F is only referenced with respect to FIG. 14. Preferably the run for the downstream section is the horizontal distance between point D and point C. Alternatively the horizontal run of the downstream transition section may be the horizontal distance between point D and point F, as seen in FIG. 14. The vertical rise of the downstream transition section 1501 is the vertical distance between point D and point C. Alternatively the vertical rise for the downstream transition section 1501 may be the vertical distance between point D and point F.

In the most preferred form the vertical rise of the upstream transition section 1500 and downstream section 1501 is substantially equal to each other. In the most preferred form the vertical rise of the upstream and downstream transition sections 1500, 1501 is exactly identical. Preferably the horizontal run of the upstream transition section 1500 is between one to two times larger than the horizontal run of said downstream transition section 1501. Most preferably the horizontal run of the upstream transition section 1500 is one and a half times larger than the horizontal run of the downstream transition section 1501.

In the alternative form where the transition sections 1500, 1501 are straight line sections, the transition sections extend upward from the horizontal manifold at an angle. The alternate upstream transition section 1500 extends upward at angle of a as shown in FIG. 14. The alternate downstream transition section 1501 extends upward at angle .beta. as shown in FIG. 14. Preferably angle .beta. is larger than angle .alpha. Preferably angle .beta. is between 1.1 and 2.5 times larger than angle .alpha. In the most preferred form angle .beta. is 1.5 times larger than angle .alpha. Preferably angles .beta. and .alpha. are between 35 degrees and 65 degrees. In the most preferred form angle .beta. is 33 degrees and angle .alpha. is 22 degrees. The ratios and relationships between the upstream and downstream transition sections described hold true for varying sized cannulae.

The upstream transition section 1500 having a shallower curve than the downstream transition is advantageous. The shallower curve of the upstream transition section 1500 guides a substantial part of the gases stream into the prongs. The downstream transition section 1501 being a sharper or steeper forces a substantial part of the gases stream to turn within the manifold before entering the prongs. The shape of the downstream transition section 1501 restricts the amount of turning of the gases stream within the prong. This allows a substantial part of the gases stream to enter the prong in a direction substantially aligned to the prongs 33, 34. The gases stream turning in the manifold 35 results in a reduced pressure drop and reduced velocity drop of the gases stream as compared to gases stream turning within the prong itself. The shallower curve or the upstream transition section 1500 and the shape of the manifold provide a larger effective diameter of the prong. This results in a lower pressure drop as compared to the gases stream turning inside the prongs. The transition sections 1500, 1501 and the shape of the transition sections forces approximately 65% of the gases stream to turn inside the manifold flow chamber. The horizontal run of the upstream transition section 1500 being larger than the run of the downstream transition section also provides for a larger effective diameter of the prong. The larger run of the upstream stream transition section allows for the gases to turn in the manifold resulting in less pressure and velocity drop. This is advantageous for the user because the correct amount of gases is delivered at the correct pressure and velocity. This results in more effective therapy being delivered to the user. While the invention is susceptible to embodiment in different forms, specific embodiments are shown in the drawings, and described in detail above. The present disclosure is to be considered an exemplification of the principles of the invention, and is not intended to limit the invention to that as illustrated and described herein.

What is claimed is:

1. A cannula arrangement comprising:
   a gases inlet manifold part configured to receive a gases flow;
   a face mount part in fluid connection with said gases inlet manifold part;
   two elongate prongs extending from the face mount part, said two elongate prongs configured for insertion into nares of a patient in an unsealed manner, the gases flow adapted to pass through said gases inlet manifold part and through said two elongate prongs;
   wherein said gases inlet manifold part comprises an inner wall having a first portion that is substantially horizontal and a second portion that is curved with respect to said first portion and toward an inlet of said two elongate prongs, said second portion at least partially facing the inlet of said two elongate prongs and configured to deflect the gases flow towards said two elongate prongs, wherein said second portion is located downstream of said first portion and connects with said first portion at a transition upstream of said two elongate prongs, the second portion of the gases inlet manifold part is located below a base of the two elongate prongs;
   wherein the second portion includes a first part and a second part, the second part is located downstream of the first part;
   wherein the two elongate prongs include a first elongate prong and a second elongate prong;
   wherein a first vertical plane intersects the first elongate prong at a center point of a top edge of the first elongate prong and the first part of the second portion, a second vertical plane intersects the second elongate prong at a center point of a top edge of the second elongate prong and the second part of the second portion, the first vertical plane and the second vertical plane are parallel to each other;
   wherein a first length of the first vertical plane that is between the center point of the top edge of the first elongate prong and the first part of the second portion is longer than a second length of the second vertical plane that is between the center point of the top edge of the second elongate prong and the second part of the second portion; and
   wherein the transition is upstream of the first vertical plane.

2. The cannula arrangement of claim 1, wherein said inner wall of said gases inlet manifold part transitions from said first portion to said second portion at a location upstream of an outlet of said gases inlet manifold part.

3. The cannula arrangement of claim 1, wherein said gases inlet manifold part connects to said face mount part at a connection portion of said gases inlet manifold part, and wherein said first portion of said inner wall of said gases inlet manifold part transitions to said second portion at a location upstream of said connection portion.

4. The cannula arrangement of claim 1, wherein the first elongate prong is positioned upstream of the second elongate prong with respect to the gases flow through said gases inlet manifold part.

5. The cannula arrangement of claim 1, wherein, in use, said second part turns upward relative to said first portion between about 30 degrees and about 90 degrees.

6. The cannula arrangement of claim 1, wherein, in use, said second portion is turns upward relative to said first portion between about 15 degrees and about 45 degrees.

7. The cannula arrangement of claim 1, wherein said gases inlet manifold part is horizontally oriented when said cannula arrangement is in use by the patient.

8. A system for delivering respiratory gases to a patient, said system comprising:
   a gas source configured to provide respiratory gases;
   a patient interface comprising said cannula arrangement of claim 1; and
   a delivery conduit configured to receive the respiratory gases from said gas source and carry the respiratory gases from said gas source to said patient interface.

9. The cannula arrangement of claim 1, wherein each of said two elongate prongs is angled between about 5 degrees and about 20 degrees inward relative to a vertical planar line which bisects said face mount part.

10. The cannula arrangement of claim 1, further comprising side straps configured to secure to a headgear strap, wherein said headgear strap is configured to secure said cannula arrangement to the patient when in use.

11. The cannula arrangement of claim 1, wherein each of said two elongate prongs is sized and/or shaped to direct the gases flow in a direction generally towards a back of a nasal passage of the patient.

12. The cannula arrangement of claim 1, wherein each of said two elongate prongs is shaped so that a velocity of gases exiting said two elongate prongs is smaller than a velocity of gases entering said two elongate prongs.

13. The cannula arrangement of claim 1, wherein each of said two elongate prongs has a rear side and a front side, said rear side closer to the patient when in use and said front side further from the patient when in use, and wherein each of said two elongate prongs curves towards the patient when said cannula arrangement is in use, and wherein each of said two elongate prongs comprises a cut-out having an elongate shape along said rear side and a top of each of said two elongate prongs.

14. The cannula arrangement of claim 1, wherein each of said two elongate prongs is shaped and/or sized so that it does not form a substantially air tight seal with the nares of the patient when in use.

15. The cannula arrangement of claim 1, wherein an outlet of the gases inlet manifold part is oriented upward toward said two elongate prongs, in use, such that the gases flow travels generally in an upward direction towards said two elongate prongs upon entrance into the face mount part.

* * * * *